United States Patent
Leach et al.

(10) Patent No.: US 9,422,253 B2
(45) Date of Patent: Aug. 23, 2016

(54) CYCLIC TRIAZO AND DIAZO SODIUM CHANNEL BLOCKERS

(71) Applicant: University of Greenwich, London (GB)

(72) Inventors: Michael Leach, Chatham (GB); Laurence Harbige, Chatham (GB); Dieter Riddall, Chatham (GB); Karl Franzmann, Chatham (GB)

(73) Assignee: UNIVERSITY OF GREENWICH (GB)

( * ) Notice: Subject to any disclaimer, the term of this patent is extended or adjusted under 35 U.S.C. 154(b) by 0 days.

(21) Appl. No.: 14/174,492

(22) Filed: Feb. 6, 2014

(65) Prior Publication Data
US 2014/0155403 A1 Jun. 5, 2014

Related U.S. Application Data

(62) Division of application No. 12/811,884, filed as application No. PCT/GB2009/050033 on Jan. 16, 2009, now Pat. No. 8,691,818.

(30) Foreign Application Priority Data

Jan. 16, 2008 (GB) .................... 0800741.1

(51) Int. Cl.
| | | |
|---|---|---|
| A61K 31/53 | (2006.01) | |
| C07D 253/075 | (2006.01) | |
| C07D 405/04 | (2006.01) | |
| C07D 253/06 | (2006.01) | |

(52) U.S. Cl.
CPC .......... *C07D 253/075* (2013.01); *C07D 253/06* (2013.01); *C07D 405/04* (2013.01)

(58) Field of Classification Search
CPC ... C07D 253/075; C07D 405/04; A61K 31/53
USPC .......................................... 514/242; 544/182
See application file for complete search history.

(56) References Cited

U.S. PATENT DOCUMENTS

| | | | |
|---|---|---|---|
| 3,637,688 A | 1/1972 | Rees et al. | |
| 4,649,139 A * | 3/1987 | Allan ................. | C07D 253/075 514/242 |
| 8,691,818 B2 * | 4/2014 | Leach ................. | C07D 253/06 514/242 |
| 8,748,599 B2 * | 6/2014 | Leach ................. | C07D 253/07 544/182 |
| 8,748,600 B2 * | 6/2014 | Leach ................. | C07D 409/06 544/182 |
| 9,000,155 B2 * | 4/2015 | Leach ................. | C07D 253/07 544/182 |
| 2004/0229873 A1 | 11/2004 | Harbige et al. | |

FOREIGN PATENT DOCUMENTS

| | | |
|---|---|---|
| EP | 0021120 | 1/1981 |
| EP | 0059987 | 9/1982 |
| EP | 0086502 A2 | 8/1983 |
| EP | 0142306 | 5/1985 |
| EP | 0459829 | 12/1991 |
| GB | 759014 | 10/1956 |
| WO | WO 03/008393 | 1/2003 |
| WO | WO 2008/007149 | 1/2008 |

OTHER PUBLICATIONS

Ulomskii, et al. "A New Approach to the Synthesis of Lamotrigine and Other 3,5-Diamino-1,2,4-Triazine Derivatives" Russian Chemical Bulletin, 54(3):726-732, 2005.

Manning, et al. "Synthesis of Stable I Sptopically Labeled Versions of Lamotrigine and its Methylated Metabolite" Journal of Labelled Compounds and Radiopharmaceuticals, 45:611-618, 2002.

Rees, et al. "Antimalarial Activities of Some 3,5-Diamino-as-triazine Derivatives" Journal of Medicinal Chemistry, (15) 8:859-861, 1972.

* cited by examiner

*Primary Examiner* — James O Wilson
*Assistant Examiner* — Ebenezer O Sackey
(74) *Attorney, Agent, or Firm* — Heslin Rothenberg Farley & Mesiti P.C.

(57) ABSTRACT

A method of treating a disorder such as epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimer's disease, Parkinson's disease, chronic inflammatory pain, neuropathic pain, migraine, bipolar disorder, mood, anxiety and cognitive disorders, schizophrenia, or trigeminal autonomic cephalalgias. The method includes administering to a subject in need thereof substituted 1,2,4-triazine compounds of formula (I):

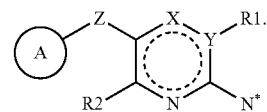

Each of A, N*, X, Y, Z, R1, and R2 is defined herein. Also disclosed are compounds of the formula and a pharmaceutical composition containing such a compound.

14 Claims, No Drawings

CYCLIC TRIAZO AND DIAZO SODIUM CHANNEL BLOCKERS

This application is a continuation of U.S. application Ser. No. 12/811,884, filed on Sep. 22, 2010, which is the National Stage of International Application No. PCT/GB2009/050033, filed on Jan. 16, 2009, claiming the priority date of United Kingdom Application No. 0800741.1, filed on Jan. 16, 2008. The contents of all the three applications are hereby incorporated by reference in their entirety.

The present invention relates to triazine compounds and cyclic diazo analogs thereof having sodium channel blocking properties, and to use of the compounds for preparation of medicaments for treatment of associated disorders.

U.S. Pat. No. 4,649,139 discloses compounds of the formula (A):

(A)

in which $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups or any adjacent two of $R^2$ to $R^6$ are linked to form a (—CH=CH—CH=CH—) group. It is disclosed that these compounds are active in the treatment of cardiac disorders, and are particularly useful in the treatment of arrhythmias.

Our patent application WO2008-007149 (published after the priority date of this application) discloses use of a compound of formula (B):

(B)

in which
$R^1$ is hydrogen (and =NH is $NH_2$), or carboxamido, $C_{2-10}$ alkenyl, $C_{1-3}$ alkyl-heterocyclyl, or $C_{3-10}$ cycloalkyl, any of which is optionally substituted by hydroxy, halogen, carboxamido, halo $C_{1-6}$ alkyl, $C_{1-6}$ alkyl or $C_{1-6}$ alkoxy;
$R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups;
(a) as voltage dependent sodium channel blockers for the treatment of disorders in mammals, and particularly epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias, especially in humans;
(b) as antifolates for the treatment of disorders in mammals, and particularly for treatment of mammalian cancers and as antimalarials against *plasmodium vivax* and *plasmodium falciparum* malaria, especially in humans.

As a $C_{1-10}$ alkyl group, $R^1$ is suitably an unsubstituted $C_{1-6}$ alkyl group, typically methyl, ethyl, i-propyl, n-propyl, i-butyl or n-butyl. Alternatively such a group may be substituted by hydroxy or halogen, such as chloro, bromo or fluoro.

As a $C_{2-10}$ alkenyl group, $R^1$ may be an unsubstituted $C_{2-6}$ alkenyl group, such as allyl.

As a $C_{3-10}$ cycloalkyl group, $R^1$ is typically cyclohexyl, optionally substituted by one or more halogen, haloalkyl or alkoxy groups, for example chloro, fluoro, trifluoromethyl, methoxy or ethoxy.

As a $C_{1-3}$alkylaryl group, $R^1$ is typically benzyl in which the phenyl group is optionally substituted by one or more halogen, haloalkyl or alkoxy groups, for example chloro, fluoro, trifluoromethyl, trifluoromethoxy, methoxy or ethoxy.

As a $C_{1-3}$alkyl-heterocyclyl, $R^1$ is suitably piperidine-methyl, optionally N-substituted, or thienyl-methyl, or furyl-methyl.

The $R^2$ to $R^6$-substituted phenyl ring suitably contains one, two or three substituents.

$R^2$ to $R^6$ when other than hydrogen are preferably selected from halogen, halo $C_{1-6}$ alkyl or alkoxy groups. Particularly preferred substitutions are 2, 3 or 2, 4 or 2,5 or or 3, 5 or 2,3,5 di- or tri-halo (especially chloro and/or fluoro).

In one class of compounds, $R^1$ is not hydrogen. In another class of compounds, $R^2$ is not hydrogen. In a further class of compounds, both $R^1$ and $R^2$ are not hydrogen.

The subject matter of WO2008-00714 is incorporated herein by reference.

The compounds of this invention have the general structure (I)

in which X and Y are each N or C with at least one of X and Y being N;
Z is a single bond or an optionally substituted linking group
R1 is hydrogen or a substituent group;
R2 is amino or a substituent group;
N* is amino when R1 is hydrogen or =NH when R1 is a substituent group; or
N* is a group NRaRb where Ra and Rb are independently H or an alkyl group; or
N* is an optionally substituted piperazinyl ring; and
A is an optionally substituted heterocyclic or carbocyclic ring system which may be linked to the triazo/diazo ring through R2 to form a fused multicyclic ring.

As a carbocyclic entity A is typically optionally substituted phenyl or naphthyl or anthracenyl or fluorenyl or adamantyl.

As a heterocyclic entity A is typically optionally substituted (benzo)thienyl or (benzo)furyl or (benzo)pyran or (iso)indole or (iso)quinoline or pyridine.

When R1 is a substituent group, suitable groups include all those disclosed in PCT/GB07/050,405 for $R^1$ in formula (B) and mentioned above, such as alkyl, hydroxyalkyl, haloalkyl, heterocyclylalkyl, alkenyl, carboxamido, benzyl, benzyl substituted by halogen, alkyl, alkoxy, hydroxyalkyl, haloalkyl or carboxamido, and the additional groups disclosed below.

Alkyl and alkoxy groups mentioned herein typically contain 1-6 or 1-4 carbon atoms, and alkenyl groups 2-4 carbon atoms.

When R2 is a substituent group other than amino, suitable groups include optionally substituted alkyl or phenyl groups When Z is linking group, it may be a carbon atom with one or two optionally substituted alkyl or phenyl groups. The alkyl groups may be linked to form a cycloalkyl group such as cyclopropyl or cyclobutyl. Z may also be an unsaturated linking group eg optionally substituted alkenyl, in which case A-Z— may be styryl.

When N* is piperazinyl, it is typically N-alkyl piperazinyl. In particular, when X is C, Y is N and R1 is H, N* may be N-methyl piperazinyl.

Quaternised salts may be formed with N atoms in the triazine/diazine ring.

Optional substituents for alkyl groups, heterocyclic or carbocyclic rings include all those disclosed in WO2008-007149 and those mentioned above, and additional groups disclosed below. The subject-matter of WO2008-007149 is hereby incorporated herein by reference.

In one special class of compounds of general formula (I), X and Y are both N, forming a triazine ring Within the general structure of formula (I) there is a group of compounds in which A is a mono, bi or tricyclic carbocyclic ring system, which may be aryl, such as phenyl, naphthyl, anthracenyl or fluorenyl; or non-aryl such as adamantyl, or a mixture of aryl and non-aryl rings. In this group the ring system A is optionally substituted with substituents listed above, or especially with one of more of halogen, such as chloro or bromo, or fluoroalkyl, such as CF3, alkoxy such as OMe or OEt, or aryloxy, such as phenoxy or benzyloxy.

In this group, typical monocylic substituents A include chlorophenyl, such as dichlorophenyl, and trichlorophenyl, for example 2,3-, 2,6- and 3,5-dichloro, and 2,3,5-trichloro; bromophenyl such as 2-bromo and 3-bromo; trifluoromethylphenyl such as di-trifluoromethyl for example 3,5-trifluoromethyl; (m) ethoxy-phenyl such as di(m)ethoxy and tri(m) ethoxy-phenyl for example 4,5 dimethoxy, 3,4,5 trimethoxy; fluoro(m)ethoxy-phenyl such as di(fluoro(m)ethoxy)-phenyl for example 2-fluoro(m)ethoxy, 4-fluoro(m)ethoxy and 2,4-di(fluoro(m)ethoxy).

When the compound of formula (I) is a triazine, the Y nitrogen may be unsubstituted or carry a substituent R1 which is suitably an alkyl group such as (m) ethyl, a fluoroalkyl group such fluoro(m)ethyl, for example —CH$_2$CHF$_2$, —CH$_2$CF$_3$.

Some typical monocyclic aromatic compounds of formula (I) where A is an optionally substituted phenyl group are:
3,5-Diamino-6-(3,4,5 trimethoxyphenyl)-1,2,4-triazine [CEN-095]
3,5-Diamino-6-(2-bromophenyl)-1,2,4-triazine [CEN-068]
3,5-Diamino-6-(3-bromophenyl)-1,2,4-triazine [CEN-069]
3,5-Diamino-6-(3,5-bistrifluoromethylphenyl)-1,2,4-triazine [CEN-092]
3,5-Diamino-6-(2,6-dichlorophenyl)-1,2,4-triazine [CEN-104]
3,5-Diamino-6-(3,4-dimethoxyphenyl)-1,2,4-triazine [CEN-115]
3,5-Diamino-6-(2-bromophenyl)-1,2,4-triazine [CEN-068]
3,5-Diamino-6-(3-bromophenyl)-1,2,4-triazine [CEN-069]
3,5-Diamino-6-(2-trifluoromethoxyphenyl)-1,2,4-triazine [CEN-056]
3,5-Diamino-6-[3-(1,1,2,2-tetrafluoroethoxy)phenyl]-1,2,4-triazine [CEN-108]
3,5-Diamino-6-[2-(1,1,2,2-tetrafluoroethoxy)phenyl]-1,2,4-triazine [CEN-137]
3,5-Diamino-6-[2,5-bis(2,2,2-trifluoroethoxy)phenyl]-1,2,4-triazine [CEN-140]
3,5-Diamino-6-[2-difluoromethoxy)phenyl]-1,2,4-triazine [CEN-142]
3,5-Diamino-6-(3-chloro-5-trifluoromethylphenyl)-1,2,4-triazine [CEN-172]
3,5-Diamino-6-[3,5 (bis-trifluoromethyl)phenyl]-1,2,4-triazine [CEN-175]
3,5-Diamino-6-(2-chloro-3-trifluoromethylphenyl)-1,2,4-triazine [CEN-176]
3,5-Diamino-6-[2-chloro-4-(methylsulphonyl)phenyl]-1,2,4-triazine [CEN-179]
3,5-Diamino-6-(2,4,6-triisopropylphenyl)-1,2,4-triazine [CEN-180]
3,5-Diamino-6-(4-tertbutylphenyl)-1,2,4-triazine [CEN-181]
3,5-Diamino-6-(4-n-butylphenyl)-1,2,4-triazine [CEN-183]
3,5-Diamino-6-(3,5-di-tert-butylphenyl)-1,2,4-triazine [CEN-187]
3,5-Diamino-6-(3,5-dimethoxyphenyl)-1,2,4-triazine [CEN-192]
3,5-Diamino-6-[3,5-bis(2,2,2-trifluoroethoxy)phenyl]-1,2,4-triazine [CEN-193]
3,5-Diamino-6-(3-chloro-2-fluoro-5-trifluoromethylphenyl)-1,2,4-triazine [CEN-197]
3,5-Diamino-6-[2,5-bis(trifluoromethyl)phenyl]-1,2,4-triazine [CEN-198]
3,5-Diamino-6-(2-chloro-3-trifluoromethylphenyl)-1,2,4-triazine [CEN-199]
3,5-Diamino-6-(5-chloro-2-trifluoromethylphenyl)-1,2,4-triazine [CEN-200]
3,5-Diamino-6-(2,3,4-trifluorophenyl)-1,2,4-triazine [CEN-206]
3,5-Diamino-6-(2-chloro-4,5-difluorophenyl)-1,2,4-triazine [CEN-207]
3,5-Diamino-6-(2,3,4,5-tetrafluorophenyl)-1,2,4-triazine [CEN-208]
3,5-Diamino-6-(2,3-dichloro-6-trifluoromethylphenyl)-1,2,4-triazine CEN209
[3,5-Diamino-6-(2,3,4,5,6-pentafluorophenyl)-1,2,4-triazine [CEN-212]
3,5-Diamino-6-(2,3,6-trichlorophenyl)-1,2,4-triazine [CEN-214]
5(3)-Amino-6-(2,3,5-trichlorophenyl)-2,3(2,5)-dihydro-3(5)-imino-2-(2,2-difluoroethyl)-1,2,4-triazine [CEN-085]
5(3)-Amino-6-(2,3,-dichlorophenyl)-2,3(2,5)-dihydro-3(5)-imino-2-(2,2,2-trifluoroethyl)-1,2,4-triazine [CEN-067]
5(3)-Amino-6-(2,3,-dichlorophenyl)-2,3(2,5)-dihydro-3(5)-imino-2-(2-isopropoxy)ethyl-1,2,4-triazine [CEN-091]
5(3)-Amino-6-phenyl-2,3(2,5)-dihydro-3(5)-imino-2-methyl-1,2,4-triazine methanesulfonate [CEN-051]
5(3)-Amino-6-(2,5-dichlorophenyl)-2,3(2,5)-dihydro-3(5)-imino-2-methyl-1,2,4-triazine [CEN-053]
5(3)-Amino-6-(3,5-dichlorophenyl)-2,3(2,5)-dihydro-3(5)-imino-2-methyl-1,2,4-triazine [CEN-059]
5(3)-Amino-6-(2-difluoromethoxyphenyl)-2,3(2,5)-dihydro-3(5)-imino-2-methyl-1,2,4-triazine [CEN-146]
5(3)-Amino-6-(2-chloro-3-trifluoromethyphenyl)-2,3(2,5)-dihydro-3(5)-imino-2-methyl-1,2,4-triazine [CEN-177]

5(3)-Amino-6-(3-chloro-2-fluoro-5-trifluoromethyphenyl)-2,3(2,5)-dihydro-3(5)-imino-2-methyl-1,2,4-triazine [CEN-202]

5(3)-Amino-6-(2-chloro-4,5-difluoro-5-phenyl)-2,3(2,5)-dihydro-3(5)-imino-2-methyl-1,2,4-triazine [CEN-204]

5(3)-Amino-6-phenyl-2,3(2,5)-dihydro-3(5)-imino-2-ethyl-1,2,4-triazine [CEN-052]

5(3)-Amino-6-(2,5-dichlorophenyl)-2,3(2,5)-dihydro-3(5)-imino-2-ethyl-1,2,4-triazine [CEN-054]

5(3)-Amino-6-(2,3,5-trichlorophenyl)-2,3(2,5)-dihydro-3(5)-imino-2-ethyl-1,2,4-triazine [CEN-055]

5(3)-Amino-6-(3,5-dichlorophenyl)-2,3(2,5)-dihydro-3(5)-imino-2-ethyl-1,2,4-triazine [CEN-060]

5(3)-Amino-6-(2-naphthyl)-2,3(2,5)-dihydro-3(5)-imino-2-ethyl-1,2,4-triazine [CEN-075]

5(3)-Amino-6-(3,4,5-trimethoxyphenyl)-2,3(2,5)-dihydro-3(5)-imino-2-ethyl-1,2,4-triazine [CEN-119]

5(3)-Amino-6-(2-chloro-3-trifluoromethyphenyl)-2,3(2,5)-dihydro-3(5)-imino-2-ethyl-1,2,4-triazine [CEN-178]

5(3)-Amino-6-(3,5-bis-tert-butylphenyl)-2,3(2,5)-dihydro-3(5)-imino-2-ethyl-1,2,4-triazine [CEN-189]

5(3)-Amino-6-(3-chloro-2-fluoro-5-trifluoromethyphenyl)-2,3(2,5)-dihydro-3(5)-imino-2-ethyl-1,2,4-triazine [CEN-203]

5(3)-Amino-6-(2-chloro-4,5-difluoro-5-phenyl)-2,3(2,5)-dihydro-3(5)-imino-2-ethyl-1,2,4-triazine [CEN-205]

5(3)-Amino-6-(3,4,5-trimethoxyphenyl)-2,3(2,5)-dihydro-3(5)-imino-2-methyl-1,2,4-triazine [CEN-101]

5(3)-Amino-6-[3,5-(bis-trifluoromethyl)phenyl]-2,3(2,5)-dihydro-3(5)-imino-2-methyl-1,2,4-triazine [CEN-099]

5(3)-Amino-6-(3-chloro-2-fluoro-5-trifluoromethyphenyl)-2,3(2,5)-dihydro-3(5)-imino-2-(2,2,3,3-tetrafluoropropyl)-1,2,4-triazine [CEN-210]

5(3)-Amino-6-(3-chloro-2-fluoro-5-trifluoromethyphenyl)-2,3(2,5)-dihydro-3(5)-imino-2-(2,2,3,3,3-pentafluoropropyl)-1,2,4-triazine [CEN-211]

In this group, typical bicyclic substituents A are naphthyl such as 1-naphthyl and 2-naphthyl or tetrahydronaphthyl, or alkylenedioxphenyl such as (m) ethylenedioxyphenyl or benzodioxolo, all of which may be optionally substituted, for example substituted by one or more halogens such as bromo, for example 6-bromonaphthyl, or fluoro, for example 2,2-difluorobenzodioxolo, or by one or more alkoxy groups such as (m) ethoxy for example 2- or 3-(m)ethoxynaphthyl, or 1,4-, 2,5- or 3,7-di(m)ethoxynaphthyl.

As before, when the compound of formula (I) with bicyclic substituents A is a triazine, the Y nitrogen may be unsubstituted or substituent R1 may suitably be an alkyl group such as (m) ethyl, a fluoroalkyl group such fluoro(m)ethyl, for example —CH$_2$CHF$_2$, —CH$_2$CF$_3$.

Some typical compounds of formula (I) where A is a bicyclic substituent are:

6-(1-Naphthyl)-1,2,4-triazine-3,5-diamine [CEN-072]

3,5-Diamino-6-(2-naphthyl)-1,2,4-triazine [CEN-073]

3,5-Diamino-6-[2-(6-bromonaphthyl)-1,2,4-triazine [CEN-096]

3,5-Diamino-6-[1-(5,6,7,8-tetrahydronaphthyl)]-1,2,4-triazine [CEN-094]

3,5-Diamino-6-[2-(3-methoxynaphthyl)-1,2,4-triazine [CEN-139]

3,5-Diamino-6-[1-(2-ethoxynaphthyl)-1,2,4-triazine [CEN-110]

3,5-Diamino-6-[2-(3-ethoxynaphthyl)-1,2,4-triazine [CEN-141]

3,5-Diamino-6-[2-(3,7-dimethoxynaphthyl)-1,2,4-triazine [CEN-143]

3,5-Diamino-6-[2-(1,4-dimethoxynaphthyl)-1,2,4-triazine [CEN-151]

3,5-Diamino-6-[1-(2,5-dimethoxynaphthyl)-1,2,4-triazine [CEN-156]

3,5-Diamino-6-[1-(2,5-dimethoxynaphthyl)-1,2,4-triazine [CEN-157]

3,5-Diamino-6-[1-(2,5-dimethoxynaphthyl)-1,2,4-triazine [CEN-158]

5(3)-Amino-6-(1-naphthyl)-2,3(2,5)-dihydro-3(5)-imino-2-ethyl-1,2,4-triazine [CEN-077]

5(3)-Amino-6-(1-naphthyl)-2,3(2,5)-dihydro-3(5)-imino-2-methyl-1,2,4-triazine [CEN-078]

5(3)-Amino-6-(2-naphthyl)-2,3(2,5)-dihydro-3(5)-imino-2-methyl-1,2,4-triazine [CEN-076]

5(3)-Amino-6-[1-(5,6,7,8-tetrahydronaphthyl)]-2,3(2,5)-dihydro-3(5)-imino-2-methyl-1,2,4-triazine [CEN-120]

5(3)-Amino-6-(2-naphthyl)-2,3(2,5)-dihydro-3(5)-imino-2-ethyl-1,2,4-triazine [CEN-075]

3,5-Diamino-6-[5-(2,2-difluorobenzodioxolo)]-1,2,4-triazine [CEN-117]

3,5-Diamino-6-[4-(2,2-difluorobenzodioxolo)]-1,2,4-triazine [CEN-070]

5(3)-Amino-6-[5-(2,2-difluorobenzodioxolo)]-dihydro-3(5)-imino-2-methyl-1,2,4-triazine [CEN-081]

3,5-Diamino-6-(3,4-ethylenedioxyphenyl)-1,2,4-triazine [CEN-109]

3,5-Diamino-6-(3,4-methylenedioxyphenyl)-1,2,4-triazine [CEN-103]

In this group, typical tricyclic substituents A are fused rings containing one or more aromatic rings such as anthracenyl or fluorenyl, or non aromatic such as adamantyl, all of which may be optionally substituted by groups proposed for monocyclic and bicyclic compounds above. Again, when the compound of formula (I) with tricyclic substituents A is a triazine, substituent R1 may be optionally substituted as proposed for monocyclic and bicyclic compounds above.

Typical tricyclic compounds of formula (I) are 6-(9-Anthracenyl)-3,5-diamino-1,2,4-triazine [CEN-118]

3,5-Diamino-6-[4-(9H-fluorenyl)-1,2,4-triazine [CEN-129]

6-Adamantyl-3,5-diamino-1,2,4-triazine [CEN-083]

6-Adamantyl-5(3)-amino-2,3(2,5)-dihydro-3(5)-imino-2-methyl-1,2,4-triazine [CEN-100]

In a class of compounds where R2 in formula (I) is not amino, R2 may suitably be a phenyl or substituted phenyl group, such as alkyl or alkoxyphenyl, or halophenyl; for example as in the illustrative triazine compounds below, which are a special group of compounds in which R2 and A are the same grouping, generating a bis-aryl structure.

As previously, triazine substituent R1 may be optionally substituted as proposed for monocyclic and bicyclic compounds above.

Illustrative bis-phenyl triazine compounds are:

3-Amino-5,6-bis(4-methylphenyl)-1,2,4-triazine [CEN-126]

3-Amino-5,6-bis(2-chlorophenyl)-1,2,4-triazine [CEN-132]

3-Amino-5,6-bis(4-methoxylphenyl)-1,2,4-triazine [CEN-127]

3-Amino-2-methyl-5,6-bis(4-methylphenyl)-1,2,4-triazine [CEN-134]

In another class of compounds of formula (I), the ring system A may be linked with substituent R2 to form a fused ring structure, as in the illustrative triazine compounds below:

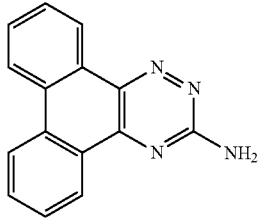
[CEN-128]

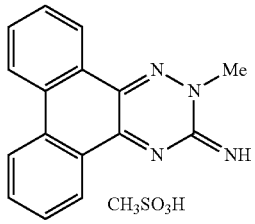
[CEN-136]

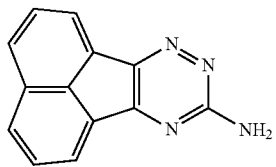
[CEN-155]

The compounds may be optionally substituted on the fused ring structure and at the R1 position as for the previously described compounds.

In a special embodiment, two structures of general formula (I) are linked together via their respective A rings. For example when A is optional substituted phenyl or naphthyl the linkage may be via a methylene or ether bridge, as in the compounds below.

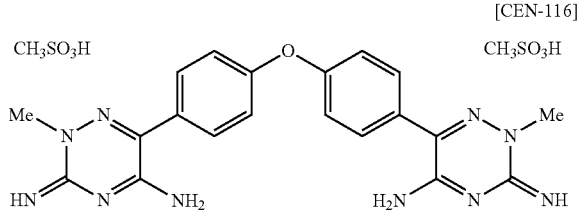
[CEN-116]

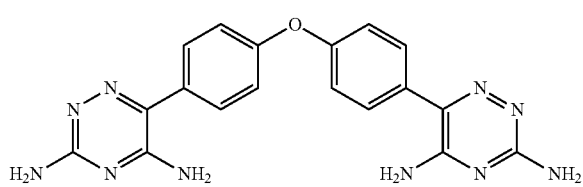
[CEN-111]

In a variation of this embodiment, a ring A structure is shared between two triazine moieties, as illustrated below.

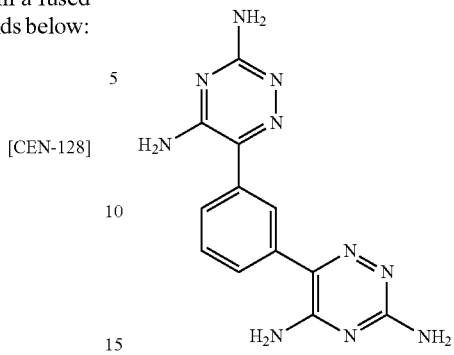
[CEN-186]

The invention includes within its scope compounds of this general bis-format in which the A ring is any other of those described herein, such as bicylic and tricylic structures already described or heterocyclic structures to be described below. Also the triazine rings may be replaced with pyrimidine and pyrazine rings described below.

In special class of compounds of formula (I), substituents on the A ring include phenyl and phenoxy, benzyl and benzyloxy, which may be optionally substituted on the phenyl ring with for example halogen or alkoxy or other substuents on phenyl rings mentioned above. This class is illustrated by the following triazines.

3,5-Diamino-6-(2-biphenyl)-1,2,4-triazine [CEN-074]
3,5-Diamino-6-(4-biphenyl)-1,2,4-triazine [CEN-082]
3,5-Diamino-6-(3-phenoxphenyl)-1,2,4-triazine [CEN-084]
3,5-Diamino-6-(4-phenoxphenyl)-1,2,4-triazine [CEN-093]
3,5-Diamino-6-(2-phenoxphenyl)-1,2,4-triazine [CEN-097]
5(3)-Amino-6-(4-phenoxyphenyl)-2,3(2,5)-dihydro-3(5)-imino-2-methyl-1,2,4-triazine [CEN-102]
5(3)-Amino-6-(2-phenoxyphenyl)-2,3(2,5)-dihydro-3(5)-imino-2-methyl-1,2,4-triazine [CEN-105]
5(3)-Amino-6-(3-phenoxyphenyl)-2,3(2,5)-dihydro-3(5)-imino-2-methyl-1,2,4-triazine [CEN-106]
3,5-Diamino-6-(3-Benzyloxyphenyl)-1,2,4-triazine [8] [CEN-123]
3,5-Diamino-6-(4-Benzyloxyphenyl)-1,2,4-triazine [CEN-131]
3,5-Diamino-6-[3-(2,4-dichlorobenzyloxyphenyl)]-1,2,4-triazine [CEN-144]
3,5-Diamino-6-(2-Benzyloxyphenyl)-1,2,4-triazine [CEN-160]
3,5-Diamino-6-[3-(2,4-trifluoromethylbenzyloxy)phenyl]-1,2,4-triazine [CEN-171]
3,5-Diamino-6-[3-(2,6-dichlorobenzyloxy)phenyl]-1,2,4-triazine [CEN-185]
3,5-Diamino-6-(3-phenylphenyl)-1,2,4-triazine [CEN-159]

In another class of compounds in general structure (I), A is an optionally substituted heterocyclic ring system, for example a monocyclic or bicyclic heterocycle with one or more oxygen or sulphur or nitrogen atoms, especially an aromatic heterocyclic ring system:

e.g. sulphur containing heterocycles such as thienyl and benzothienyl, optionally substituted as for previously described mono and bicyclic A structures, for example by halogen, alkyl or alkoxy, especially by 1, 2 or 3 chlorine or bromine atoms.

Typical compounds of this class are:
3,5-Diamino-6-(2-thienyl)-1,2,4-triazine [CEN-057]
3,5-Diamino-6-(3-thienyl)-1,2,4-triazine [CEN-064]
3,5-Diamino-6-[3-(2,5 dichlorothienyl)]-1,2,4-triazine [CEN-071]

3,5-Diamino-6-[2-(3,4,5 trichlorothienyl)]-1,2,4-triazine [CEN-079]
5(3)-Amino-6-(2-thienyl)-2,3(2,5)-dihydro-3(5)-imino-2-methyl-1,2,4-triazine [CEN-061]
5(3)-Amino-6-(2-thienyl)-2,3(2,5)-dihydro-3(5)-imino-2-ethyl-1,2,4-triazine [CEN-062]
5(3)-Amino-6-[3-(2,5-dichlorothienyl)]-2,3(2,5)-dihydro-3(5)-imino-2-methyl-1,2,4-triazine [CEN-080]
5(3)-Amino-6-{2-(3,4,5-trichloro)thienyl}-2,3(2,5)-dihydro-3(5)-imino-2-methyl-1,2,4-triazine [CEN-194]
5(3)-Amino-6-{2-(3,4,5-trichloro)thienyl}-2,3(2,5)-dihydro-3(5)-imino-2-ethyl-1,2,4-triazine [CEN-195]
3,5-Diamino-6-[2-(4,5-dibromothienyl)]-1,2,4-triazine [CEN-122]
3,5-Diamino-6-[2-(5-bromothienyl)]-1,2,4-triazine [CEN-124]
3,5-Diamino-6-[2-(3-bromothienyl)]-1,2,4-triazine [CEN-125]
3,5-Diamino-6-[2-(5-chlorothienyl)]-1,2,4-triazine [CEN-138]
3,5-Diamino-6-[2-(benzo[b]thiophenyl)]-1,2,4-triazine [CEN-113]
3,5-Diamino-6-[2-(3-chlorobenzo[b]thiophenyl)]-1,2,4-triazine [CEN-114]

e.g. oxygen containing heterocycles such as furyl, phenylfuryl and benzopyranyl, optionally substituted as for previously described mono and bicylic A structures, for example by halogen, alkyl or alkoxy, especially by 1, 2 or 3 chlorine or bromine atoms.

Typical compounds of this class are:
3,5-Diamino-6-[2-(5-phenylfuryl)]-1,2,4-triazine [CEN-107]
3,5-Diamino-6-[2-(4,5-dibromofuryl)]-1,2,4-triazine [CEN-121]
3,5-Diamino-6-[3-(2-oxo-2H-1-benzopyranyl)-1,2,4-triazine [CEN-133]
5(3)-Amino-6-[2-(4,5-dibromofuryl)]-2,3(2,5)-dihydro-3(5)-imino-2-methyl-1,2,4-triazine methanesulfonate [CEN-135]

e.g. nitrogen containing heterocycles, such as pyridyl, indolyl, quinolyl, isoquinolyl, optionally substituted as for previously described mono and bicylic A structures, for example by halogen, alkyl or alkoxy, especially by 1, 2 or 3 chlorine or bromine atoms, such as chloropyridyl, anddichloropyridyl. The nitrogen containing heterocycles may also optional be N-substutued by alkyl such as methyl, or substutued by phenoxy or phenylthio, with the phenyl optionally substutued by halogen such as chloro.

Typical compounds of this class are:
3,5-Diamino-6-[3-(2-chloropyridyl)]-1,2,4-triazine [CEN-164]
3,5-Diamino-6-[2-(6-chloropyridyl)]-1,2,4-triazine [CEN-166]
3,5-Diamino-6-[3-(2-phenoxypyridyl)]-1,2,4-triazine [CEN-167]
3,5-Diamino-6-[3-(5,6-dichloropyridyl)]-1,2,4-triazine [CEN-168]
3,5-Diamino-6-(2-quinolyl)-1,2,4-triazine [CEN-173]
3,5-Diamino-6-[3-(2,6-dichloropyridyl)]-1,2,4-triazine [CEN-174]
3,5-Diamino-6-[3-(6-chloro-pyridyl)]-1,2,4-triazine [CEN-191]

In the heterocyclic systems, optional substituents for the A ring include those disclosed for the carbocyclic A rings. As previously, in triazines, substituent R1 may be optionally substituted as proposed for monocyclic and bicylic compounds above In an analogous manner to the previously described bisphenyl triazine compounds, the invention includes bis-heterocycle compounds as illustrated by the compound 3-Amino-5,6-bis(2-furyl)-1,2,4-triazine [CEN-196]

In another class of compounds within general structure (I), Z is entity other than a single bond. Within this class there is a group of compounds in which Z is an optionally substituted cycloalkyl ring eg a cyclohexyl ring, interposed between the structure A and the XY ring, or in which Z is an alkenyl bridge, optionally substituted by, for example alkyl such as methyl, or by cyano, as in the illustrative compound
3,5-Diamino-6-[E-2-(3-phenyl)propenyl]-1,2,4-triazine [CEN-112]

Also within this class of compounds with a bridge between the A ring and the XY ring, there is group of compounds represented by general formula (V)

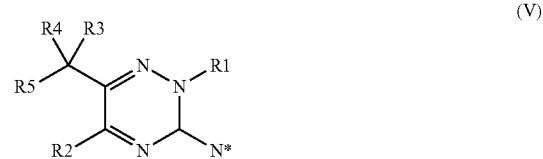

(V)

in which the R3, R4 and R5 groups are independently hydrogen, or alkyl, or a ring system A as defined for formula (I), with the proviso that only one of R3, R4 and R5 is hydrogen. Suitably, at least one of R3, R4 and R5 is a ring system A. R1, R2 and N* are as previously defined.

Suitable alkyl groups for R3, R4 or R5 include methyl, ethyl, propyl and butyl. Alkyl groups may be substituted, for example, by halogen or alkoxy groups.

When one or more of R3, R4 and R5 is a heterocyclic or carbocyclic ring system as proposed for ring A, typical examples are phenyl, naphthyl, xanthyl, as representatives of monocyclic, bicylic and tricylic moieties mentioned previously. Optional substituents as proposed for ring A may be present, such as halogens (chloro, fluoro, bromo) and alkoxy, for example methoxy.

One or more of the R3, R4 and R5 substituents may be connected to the common carbon atom via an oxygen atom, for example, as an optionally substituted phenoxy group.

Typical triazine compounds of formula (V) are shown below for illustration of this group.
3,5-Diamino-6-(diphenylmethyl)-1,2,4-triazine [R3=H, R4=R5=Ph [CEN-130]
3,5-Diamino-6-(1,1-diphenylethyl)-1,2,4-triazine [R3=Me, R4=R5=Ph] [CEN-147]
5(3)-Amino-6-(1,1-diphenylethyl)-2,3(2,5)-dihydro-3(5)-imino-2-methyl-1,2,4-triazine [CEN-149]
3,5-Diamino-6-(triphenylmethyl)-1,2,4-triazine [R3=R4=R5=Ph] [CEN-153]
3,5-Diamino-6-(1-cyclopentyl-1-phenyl)-1,2,4-triazine [R3=cyclopentyl, R4=Ph, R5=H] [CEN-163]
3,5-Diamino-6-[1-(6-methoxynaphthalene)methyl]-1,2,4-triazine [R3=6-methoxynaphthyl, R4=Me, R5=H] [CEN-165]
3,5-Diamino-6-(1-propylbutyl)-1,2,4-triazine [R3=R4=propyl, R5=H] [CEN-170]
3,5-Diamino-6-[1-(6-methoxynaphthalene)ethyl]-1,2,4-triazine [R3+R4=xanthyl, R5=H][CEN-182]
3,5-Diamino-6-(1-isopropyl-1-phenylmethy)-1,2,4-triazine [R3=isopropyl, R4=phenyl, R5=H] [CEN-201]
3,5-Diamino-6-[1,1 bis-(4-chlorophenyl)methyl]-1,2,4-triazine [R3=R4=4-chlorophenyl, R5=H] [CEN-213]

3,5-Diamino-6-{1-(4-chlorophenoxy)-1-methyl}ethyl-1,2,
4-triazine tosylate [CEN 215]

In a modification of formula (V), two of R3, R4 and R5, as two alkyl groups are linked together to form a cycloalkyl group, such as cyclopropyl, cyclobutyl, cyclopentyl or cyclohexyl group. Illustrative of this modification are the compounds 5(3)-Amino-6-{1-[1-(4-chlorophenyl)]cyclopentyl}-2,3(2, 5)-dihydro-3(5)-imino-2-methyl-1,2,4-triazine [CEN-150]

3,5-Diamino-6-[1-(4-chlorophenyl)-1-cyclopenty]-1,2,4-triazine [CEN-148]

3,5-Diamino-6-[1-(4-chlorophenyl)-1-cyclohexyl]-1,2,4-triazine [CEN-145]

3,5-Diamino-6-[1-(4-chlorophenyl)-1-cyclobuty]-1,2,4-triazine [CEN-152]

3,5-Diamino-6-[1-(4-chlorophenyl)-1-cyclopropyl]-1,2,4-triazine [CEN-154]

As previously, in triazines, substituent R1 may be optionally substituted as proposed for monocyclic and bicylic triazine compounds above.

In one special class of compounds of general structure (I), X is N and Y is H, forming a pyrazine ring.

Within that class typical compounds are 2,6-Diamino-3-(2,3,5-trichlorophenyl)pyrazine [CEN-86]
2,6-Diamino-3-(2,3-dichlorophenyl)pyrazine [CEN-87]
2,6-Diamino-3-(2-naphthyl)pyrazine [CEN-88]
2,6-Diamino-3-(2,2-difluorobenzodioxol-4-yl)pyrazine [CEN-89]

The optional substituents for the A ring and XY ring in pyrazines of formula (I) may include any of those proposed for the triazine compounds previously discussed. Additionally pyrazines may be N-alkylated, typically N-methylated, at the X position as illustrated by the compound

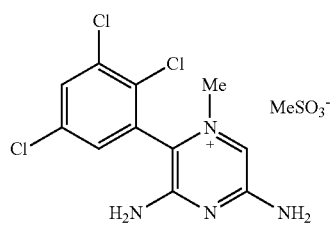

CEN-090

In another special class of compounds of general structure (I), X is H and Y is N, forming a pyrimidine ring.

Within that class typical compounds are 2,4-Diamino-5-(2,3-dichlorophenyl)pyrimidine, [CEN-41]
4(2)-Amino-5-(2,3-dichlorophenyl)-2,4(2,5)-dihydro-2(4)-imino-1-methylpyrimidine [CEN-42]
4(2)-Amino-5-(2,3-dichlorophenyl)-2,4(2,5)-dihydro-2(4)-imino-1-methylpyrimidine [CEN-43]
2,4-Diamino-5-(2,3,5-trichlorophenyl)pyrimidine [CEN-047]

The optional substituents for the A ring and XY ring in pyrmidines of formula (I) may include any of those proposed for the triazine compounds previously discussed. Additionally pyrimidines may be alkylated, typically methylated or ethylated, at the X position as illustrated by the compound 2,4-Diamino-5-(4-chlorophenyl)-6-ethyl-pyrimidine [CEN-048]

The invention also includes use of piperazinyl pyrimidines of formula (I) as illustrated by

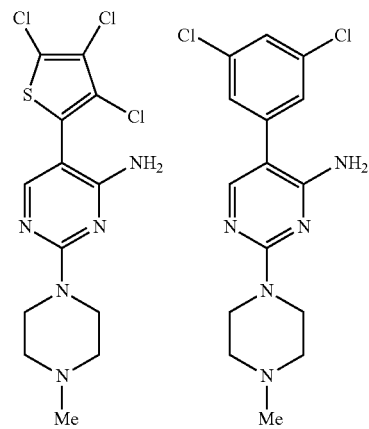 [SMILES: CN1CCN(c2ncc(-c3sc(Cl)c(Cl)c3Cl)c(N)n2)CC1 ; CN1CCN(c2ncc(-c3cc(Cl)cc(Cl)c3)c(N)n2)CC1]

which are prepared using the procedures set out in EP-A-0372934.

Further pyrimidine and pyrazine compounds of formula (I) are substituted at R1 and R2, and have various A rings, as disclosed above for triazines of formula (I).

Further compounds that show variants of the substitution pattern within the scope of formula (I) are illustrated by compounds which may be prepared by procedure (4) below

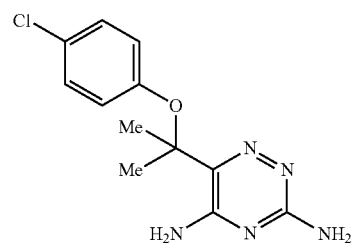

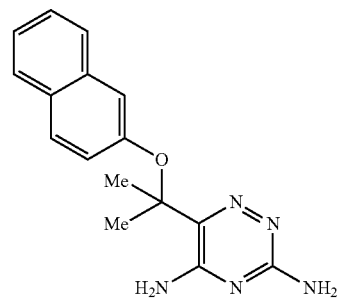

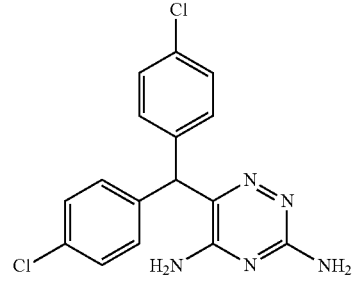

-continued

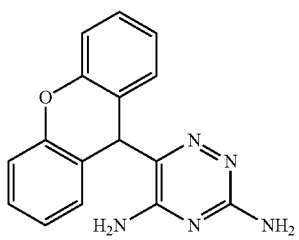

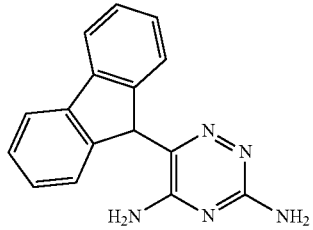

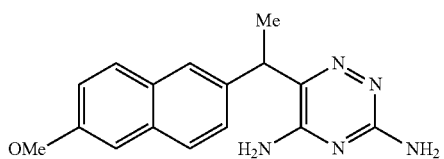

Or illustrated by compounds which may be prepared by procedure (3) below

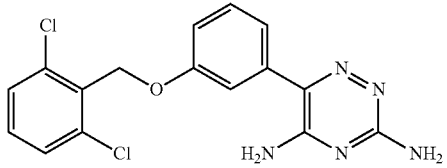

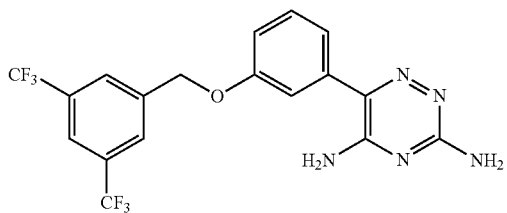

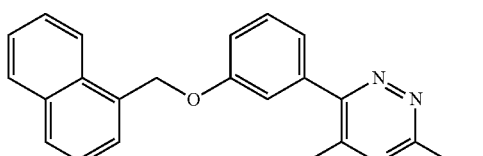

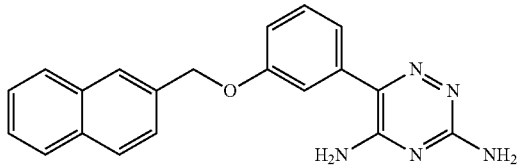

Or illustrated by compounds which may be prepared by procedure (1) below

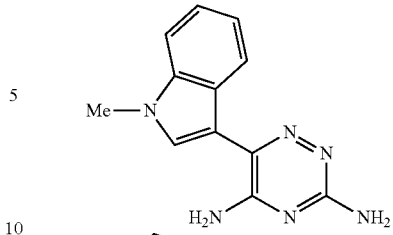

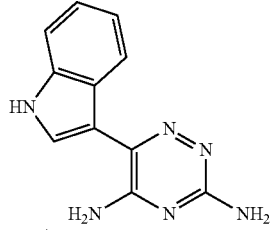

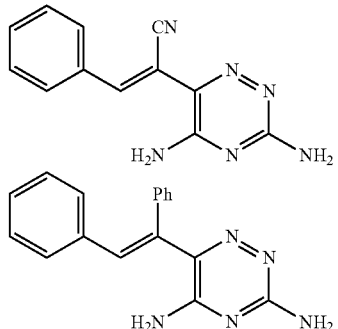

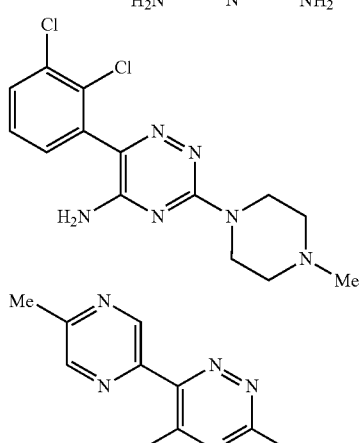

The use of salts of the compounds of formula (I) forms an aspect of this invention. Preferred salts are pharmaceutically acceptable acid addition salts. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzene-sulphonic, glutamic, naphthoic, and isethionic acids. Ethanesulfonate, malate, mandalate, benzoate, and salicylate salts are also suitable.

In preparation of the compounds of formula (I), the compound or its salt may be obtained as a solvate of the reaction solvent or crystallisation solvent or a component thereof. Use of such solvates forms another aspect of this invention. Suitable pharmaceutically acceptable solvates include hydrates.

Certain compounds of structure (I) have chiral centres and may occur as racemates, racemic mixtures and as individual enantiomers or diastereomers. All such isomeric forms are included within the present invention. Also included within the scope of the invention are all geometric isomers of the compound of formula (I) whether as individual isomers or mixtures thereof. Thus compounds of structure (I) in the trans and cis configuration form a further aspect of the invention; also all other tautomeric form of structure (I), including mixtures thereof. Furthermore, some of the crystalline forms of the compounds of structure (I) may exist as polymorphs, which are all included in the present invention.

Certain compounds of formula (I) may be prepared by the procedures disclosed in the above-mentioned U.S. Pat. No. 4,649,139, the entire disclosure of which is incorporated herein by reference.

Certain compounds of formula (I) may also be prepared by methods disclosed in EP 0 021 121 A, the entire disclosure of which is incorporated herein by reference.

The preparation of specific compounds mentioned above is illustrated later in this specification. Related compounds within the scope of the invention may be prepared by obvious or routine variations of the disclosed processes, using appropriate starting materials to introduce the desired substituents and moieties of compounds within the scope of formula (I).

Salts of compounds of formula (I) may be obtained by the presence of a residual acid in the preparative process. Alternatively salts may be prepared by mixing the compound of formula (I) as the free base with a pharmaceutically acceptable acid in a suitable solvent, and removing the solvent to recover the salt, or crystallising the salt from the solvent.

In a further aspect, the present invention provides pharmaceutical compositions for the treatment of disorders such as epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria; comprising a compound of formula (I), or a pharmaceutically acceptable salt or solvate thereof, in admixture with a pharmaceutically acceptable carrier.

The compounds of formula (I) will be present in the compositions of the present invention in an effective unit dosage form, that is to say in an amount sufficient to be effective against the disorders in vivo.

The pharmaceutically acceptable carriers present in the compositions of the present invention may be materials conventionally used for the purpose of administering the medicament.

These may be liquid or solid materials, which are otherwise inert or medically acceptable and are compatible with the active ingredients.

These pharmaceutical compositions may be given orally or parenterally, for example as a suppository, ointment, cream, powder or trans-dermal patch. However, oral administration and intravenous injection of the compositions are preferred.

For oral administration, fine powders or granules will contain diluting, dispersing and/or surface active agents, and may be presented in draught, in water or in a syrup, in capsules or sachets in the dry state or in non-aqueous suspension wherein suspending agents may be included, or in a suspension in water or syrup. Where desirable or necessary, flavouring, preserving, suspending, or thickening agents can be included. Dry powders or granules may be compressed to form a tablet or contained in a capsule.

For injection, the compounds may be presented in sterile aqueous injection solutions which may contain anti-oxidants or buffers.

The free base or a salt or solvate thereof may also be administered in its pure form unassociated with other additives in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of compound of formula I which is effective at such dosage or as a multiple of the same, for instance units containing 5 mg to 500 mg, usually around 10 mg to 250 mg.

The pharmaceutical compositions of the present invention may be prepared by the admixture of a compound of formula (I) with a pharmaceutically acceptable carrier. Conventional pharmaceutical excipients may be admixed as required. Examples of suitable formulations are give in the above-mentioned U.S. Pat. No. 4,649,139.

The present invention provides a method of treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria; by the administration of a non-toxic effective amount of a compound of formula (I) or a pharmaceutically acceptable salt or solvate thereof, or a composition as hereinbefore defined.

The present invention also provides of a compound of formula (I) or a pharmaceutically acceptable salt or solvate thereof, or a composition as hereinbefore defined. for, or for the preparation of a medicament for, treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

As indicated above, the compounds of formula (I) are generally useful in treating such disorders by oral administration or intravenous injection.

The compounds of formula (I) are normally administered at a dose of from 0.01 mg/kg to 20 mg/kg per day, preferably 0.1 to 5.0 mg/kg per day.

In view of the known use in humans of structurally similar compounds such as lamotrigine, and oher known compounds within the scope of formula (I), no major toxicity problems are anticipated in use of compounds of formula (I). However appropriate testing procedures should be carried out before clinical use.

The methodology for preparation of illustrative compounds of formula (I) and other compounds used in testing, is reported below. This may be adapted to prepare analogous compounds with additional or alternative substituents or moieties mentioned herein.

In the procedures below all melting points are in ° C.

3,5-Diamino-6-Aryl-1,2,4-triazine compounds—Procedure [1]

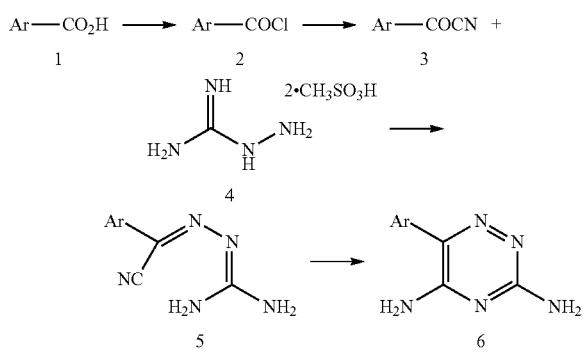

3,4-Dimethoxybenzoyl cyanide (3; Ar=3,4-dimethoxyphenyl)

Procedure A

A well stirred mixture [paddle stirrer] of 3,4-dimethoxybenzoyl chloride [AcrosOrganics] (14.05 g; 0.070 mol), dry toluene (32 cm$^3$), dry acetonitrile (8.0 cm$^3$), copper I cyanide (8.5; 0.095 mol) and Celite (5 g) was heated under reflux until no acid chloride remained (~1.5 hrs). The dark reaction mixture was cooled to ~70° and diluted with toluene (150 cm$^3$). After stirring for an additional ~30 minutes, the resulting slurry was filtered through a bed of chromatographic silica gel (~2.5 cm) and the pale yellow filtrate evaporated in vacuo to constant weight to give the title compound as a lemon yellow solid.

Yield=11.41 g (85.3%)
Mpt=143-145° C.
The product was used directly in next stage.
Aminoguanidine bismesylate 4

To a stirred solution of 99.5% methanesulphonic acid [Aldrich] (422 g; 4.40 mol) in methanol (720 cm$^3$) at 40° was added portionwise over 30 minutes aminoguanidine bicarbonate [Aldrich] (272.0 g; 2.00 mol). When the addition was complete, the solution was stirred until the temperature had fallen to ~40° and then treated slowly with cold ether (500 cm$^3$). During the addition, colourless needles started to deposit. The resulting slurry was stood at 0° for 4 hrs, filtered and the product washed with cold ether and dried overnight in vacuo at 50°. Yield=528 g (99.25%), mpt=149-150°
(Lit: WO/2004/026845; 147.5°)
Schiff's Base, cyanohydrazone (5, Ar=3,4-dimethoxyphenyl)

Procedure A

To a stirred solution of aminoguanidine bismesylate (14.0 g; 0.053 mol) in 99.5% methanesulphonic acid (22 g) at 65-70° was added dropwise a warm solution of 3,4-dimethoxybenzoyl cyanide (5.7 g; 0.030 mol) in acetonitrile (30 cm$^3$) over ~25 minutes. The mixture was then stirred at 68° until a sample gave a clear solution in water (~2.5 hrs) and then poured onto crushed ice/water (125 g) giving a pale yellow precipitate. The stirred mixture was neutralised (pH 8-9) with 48% sodium hydroxide (19.0 cm$^3$) giving a bright yellow precipitate. The product was filtered, washed with cold water and dried in vacuo at 45°.

Yield=6.21 g (83.8%)
Mpt=98-100° C.
TLC [SiO$_2$ plate, 10% methanol in chloroform], R$_f$=0.52
The product was used directly in the next stage.

3,5-Diamino-6-(3,4-dimethoxyphenyl)-1,2,4-triazine
[6, Ar=3,4-dimethoxyphenyl][CEN-115]

A solution of the above cyanohydrazone (6.21 g) in propan-1-ol (70 cm$^3$) was treated with 20% sodium ethoxide solution in ethanol (1.5 cm$^3$) to adjust the pH to 9-10 and the mixture heated under reflux until no starting material remained (1.5 hrs). During this time, the starting material went partially into solution and a bright yellow crystalline solid was deposited. After standing at room temperature, the product was filtered off, washed with cold acetone and dried at 45° in vacuo giving the title compound. (6.06 g; 99.3%)
Mpt=288-290° C.
TLC [SiO2 plate, 10% methanol in chloroform], R$_f$=0.35
The following compounds were prepared using the above procedures:

3,5-Diamino-6-(3,4,5 trimethoxyphenyl)-1,2,4-triazine [CEN-095]

Obtained from 3,4,5-trimethoxybenzoyl chloride [Fluka] using similar methodology to that employed for example [CEN-115] as pale orange-buff prisms, melting point 309-311° C. (decomp.), tlc (20% methanol+chloroform), R$_f$=0.57

3,5-Diamino-6-(2-thienyl)-1,2,4-triazine [CEN-057]

Obtained from 2-thienylcarboxylic acid using similar methodology to that employed for example [CEN-115] as dark gold plates, melting point 271-272° C. (decompes), tlc (10% methanol+chloroform), R$_f$=0.58

3,5-Diamino-6-(3-thienyl)-1,2,4-triazine [CEN-064]

Obtained from 3-thienylcarboxylic acid using similar methodology to that employed for example [CEN-115] as a beige powder, melting point 199-201 (decomp.), tlc (10% methanol+chloroform), R$_f$=0.44

3,5-Diamino-6-(2-bromophenyl)-1,2,4-triazine [CEN-068]

Obtained from 2-bromobenzoic acid using similar methodology to that employed for example [CEN-115] as a pale cream solid, melting point 198-200° C., tlc (20% methanol+chloroform), R$_f$=0.65

3,5-Diamino-6-(3-bromophenyl)-1,2,4-triazine [CEN-069]

Obtained from 3-bromobenzoic acid using similar methodology to that employed for example [CEN-115] as a pale yellow prisms, melting point 221-222° C., tlc (20% methanol+chloroform), R$_f$=0.52

3,5-Diamino-6-[3-(2,5 dichlorothienyl)]-1,2,4-triazine [CEN-071]

Obtained from 2,5-dichlorothiophene-3-carboxylic acid (Alfaaesar) using similar methodology to that employed for example [CEN-115] as dark gold plates, melting point 190-192°, tlc (20% methanol+chloroform), $R_f$=0.68

3,5-Diamino-6-[2-(3,4,5 trichlorothienyl)]-1,2,4-triazine [CEN-079]

Obtained from 3,4,5-trichlorothiophene-2-carboxylic acid [Alfaaesar] using similar methodology to that employed for example [CEN-115] as pale yellow-tan solid, melting point 263-265°, tlc (10% methanol+chloroform), $R_f$=0.33

The toluene sulphonate salt was prepared by standard procedure as small colourless prisms, mpt=208-210°

6-(1-Naphthyl)-1,2,4-triazine-3,5-diamine [CEN-072]

Obtained from 1-naphthoic acid using similar methodology to that employed for example [CEN-115] as pale yellow prisms, melting point 194-196°, tlc (20% methanol+chloroform), $R_f$=0.60

3,5-Diamino-6-(2-naphthyl)-1,2,4-triazine [CEN-073]

Obtained from 2-naphthoic acid using similar methodology to that employed for example [CEN-115] as pale cream plates, melting point 215-216°, tlc (20% methanol+chloroform), $R_f$=0.66

3,5-Diamino-6-[2-(6-bromonaphthyl)-1,2,4-triazine [CEN-096]

Obtained from 6-bromo-2-naphthoic acid [Alfaaesar] using similar methodology to that employed for example [CEN-115] as cream plates, melting point 260-262°, tlc (20% methanol+chloroform), $R_f$=0.64

3,5-Diamino-6-(2-biphenyl)-1,2,4-triazine [CEN-074]

Obtained from 2-biphenyl carboxylic acid [AcrosOrganics] using similar methodology to that employed for example [CEN-115] as a colourless solid, melting point 222-224°, tlc (10% methanol+chloroform), $R_f$=0.57

3,5-Diamino-6-(4-biphenyl)-1,2,4-triazine [CEN-082]

Obtained from 4-biphenyl carboxylic acid [Alfaaesar] using similar methodology to that employed for example [CEN-115] as pale yellow prisms, melting point 282-284°, tlc (10% methanol+chloroform), $R_f$=0.55

3,5-Diamino-6-(2-phenoxphenyl)-1,2,4-triazine [CEN-097]

Obtained from 2-phenoxybenzoic acid [Aldrich] using similar methodology to that employed for example [CEN-115] as pale yellow prisms, melting point 200-202°, tlc (10% methanol+chloroform), $R_f$=0.32

3,5-Diamino-6-(3-phenoxphenyl)-1,2,4-triazine [CEN-084]

Obtained from 3-phenoxybenzoic acid [Aldrich] using similar methodology to that employed for example [CEN-115] as a pale yellow solid, melting point 152-153°, tlc (20% methanol+chloroform), $R_f$=0.57

3,5-Diamino-6-(4-phenoxphenyl)-1,2,4-triazine [CEN-093]

Obtained from 4-phenoxybenzoic acid [Aldrich] using similar methodology to that employed for example [CEN-115] as pale yellow prisms, melting point 266-267°, tlc (10% methanol+chloroform), $R_f$=0.33

3,5-Diamino-6-(3,5-bistrifluoromethylphenyl)-1,2,4-triazine [CEN-092]

Obtained from 3,5-bistrifluoromethylbenzoic acid [Aldrich] using similar methodology to that employed for example [CEN-115] as off-white prisms, melting point 213-215°, tlc (20% methanol+chloroform), $R_f$=0.69

3,5-Diamino-6-[1-(5,6,7,8-tetrahydronaphthyl)-1,2,4-triazine [CEN-094]

Obtained from 5,6,7,8-tetrahydronaphthalene-1-carboxylic acid [Shanghai FWD Chemicals Limited, China] using similar methodology to that employed for example [CEN-115] as very pale cream prisms, melting point 202-204°, tlc (10% methanol+chloroform), $R_f$=0.50

3,5-Diamino-6-(3,4-methylenedioxyphenyl)-1,2,4-triazine [CEN-103]

Obtained from piperonylic acid [AcrosOrganics] using similar methodology to that employed for example [CEN-115] as pale cream needles, melting point 217-218°, tlc (20% methanol+chloroform), $R_f$=0.48

3,5-Diamino-6-(2,6-dichlorophenyl)-1,2,4-triazine [CEN-104]

Obtained from 2,6-dichlorobenzoic acid using similar methodology to that employed for example [CEN-115] as pale beige prisms, melting point 160-162°, tlc (10% methanol+chloroform), $R_f$=0.46

3,5-Diamino-6-[2-(5-phenyl furyl)]-1,2,4-triazine [CEN-107]

Obtained from 5-phenyl-2-furoic acid [Fluorochem] using similar methodology to that employed for example [CEN-115] as a dull yellow solid, melting point 247-249°, tlc (20% methanol+chloroform), $R_f$=0.68

3,5-Diamino-6-(3,4-ethylenedioxyphenyl)-1,2,4-triazine [CEN-109]

Obtained from 3,4-(ethylenedioxy)benzoic acid [Apollo Scientific Ltd] using similar methodology to that employed for example [CEN-115] as dark cream prisms, melting point 220-222°, tlc (10% methanol+chloroform), $R_f$=0.28

Bis-[3,5-Diamino-6-(4-ARYL)-1,2,4-triazine] [CEN-111]

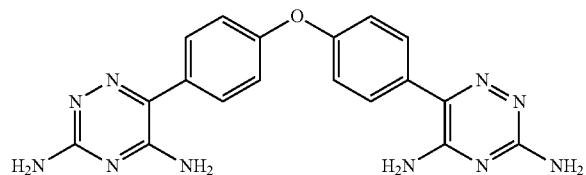

Obtained from 4,4'-oxybis(benzoic acid) [Aldrich] using similar methodology to that employed for example [CEN-115] as a pale cream solid, melting point >360° (darkens at ~300°), tlc (20% methanol+chloroform), $R_f$=0.22

3,5-Diamino-6-[E-2-(3-phenyl)propenyl]-1,2,4-triazine [CEN-112]

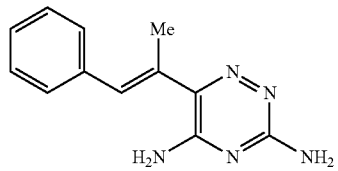 [SMILES: C/C(=C\c1ccccc1)c1nnc(N)nc1N]

Obtained from (E)-alpha-phenylcinnamic acid [AcrosOrganics] using similar methodology to that employed for example [CEN-115] as a pale yellow solid, melting point 212-213°, tlc (10% methanol+chloroform), $R_f$=0.55

3,5-Diamino-6-[2-(benzo[b]thiophenyl)]-1,2,4-triazine [CEN-113]

Obtained from benzo[b]thiophene-2-carboxylic acid [Acros Organics] using similar methodology to that employed for example [CEN-115] as dark cream prisms, melting point 344-345° (decomp.), tlc (10% methanol+chloroform), $R_f$=0.44

3,5-Diamino-6-[2-(3-chlorobenzo[b]thiophenyl)]-1,2,4-triazine [CEN-114]

Obtained from 3-chlorobenzo[b]thiophene-2-carboxylic acid [Fluorochem] using similar methodology to that employed for example [CEN-115] as pale cream prisms, melting point 318-320° (decomp.), tlc (10% methanol+chloroform), $R_f$=0.30

6-(9-Anthracenyl)-3,5-diamino-1,2,4-triazine [CEN-118]

Obtained from anthracene-9-carboxylic acid [Alfa Aesar] using similar methodology to that employed for example [CEN-115] as a light grey powder, melting point 350-352° (decomp.), tlc (10% methanol+chloroform), $R_f$=0.43

3,5-Diamino-6-[2-(4,5-dibromofuryl)]-1,2,4-triazine [CEN-121]

Obtained from 4,5-dibromo-2-furoic acid [Aldrich] using similar methodology to that employed for example [CEN-115] as a pale cream solid, melting point 272-275° (effervesce.), tlc (10% methanol+chloroform), $R_f$=0.13

3,5-Diamino-6-[2-(4,5-dibromothienyl)]-1,2,4-triazine [CEN-122]

Obtained from 4,5-dibromothiophene-2-carboxylic acid [Alfa Aesar] using similar methodology to that employed for example [CEN-115] as a pale cream solid, melting point 318-320° (effervesce.), tlc (10% methanol+chloroform), $R_f$=0.22

3,5-Diamino-6-[2-(5-bromothienyl)]-1,2,4-triazine [CEN-124]

Obtained from 5-bromothiophene-2-carboxylic acid [Aldrich] using similar methodology to that employed for example [CEN-115] as a pale cream solid, melting point 265-268° (decomp.), tlc (10% methanol+chloroform), $R_f$=0.42

3,5-Diamino-6-[2-(3-bromothienyl)]-1,2,4-triazine [CEN-125]

Obtained from 3-bromothiophene-2-carboxylic acid [Aldrich] using similar methodology to that employed for example [CEN-115] as pale cream plates, melting point 215-217°, tlc (10% methanol+chloroform), $R_f$=0.42

3,5-Diamino-6-[4-(9H-fluorenyl)-1,2,4-triazine [CEN-129]

Obtained from 9H-fluorene-4-carboxylic acid [Acros Organics] using similar methodology to that employed for example [CEN-115] as cream prisms plates, melting point 240-242°, tlc (10% methanol+chloroform), $R_f$=0.38

3,5-Diamino-6-[3-(2-oxo-2H-1-benzopyranyl)-1,2,4-triazine [CEN-133]

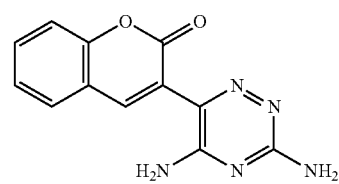 [SMILES: Nc1nnc(-c2cc3ccccc3oc2=O)c(N)n1]

Obtained from coumarin-3-carboxylic acid [Fluka] using similar methodology to that employed for example [CEN-115] as a tan crystalline solid, melting point >350° (decomp.), tlc (25% methanol+chloroform), $R_f$=0.27

3,5-Diamino-6-[2-(5-chlorothienyl)]-1,2,4-triazine [CEN-138]

Obtained from 5-chlorothiophene-2-carboxylic acid [Acros Organics] using similar methodology to that employed for example [CEN-115] as dull cream plates, melting point 312-314° (decomp.), tlc (20% methanol+chloroform), $R_f$=0.57

3,5-Diamino-6-(2-trifluoromethoxyphenyl)-1,2,4-triazine [CEN-056]

Obtained from 2-trifluoromethoxybenzoic acid [Fluorochem] using similar methodology to that employed for example [CEN-115] as a pale cream solid, melting point 148-150°, tlc (10% methanol+chloroform), $R_f$=0.58

3,5-Diamino-6-[4-(2,2-difluorobenzodioxolo)]-1,2,4-triazine [CEN-070]

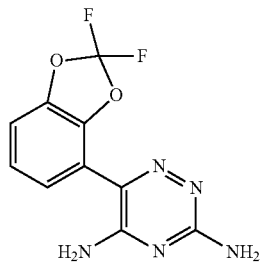 [SMILES: Nc1nnc(-c2cccc3c2OC(F)(F)O3)c(N)n1]

Obtained from 2,2-Difluorobenzodioxole-4-carboxylic acid [Apollo Scientific Ltd] using similar methodology to that employed for example [CEN-115] as a pale yellow solid, melting point 200-201°, tlc (20% methanol+chloroform), $R_f$=0.63

3,5-Diamino-6-[5-(2,2-difluorobenzodioxolo)]-1,2,4-triazine [CEN-117]

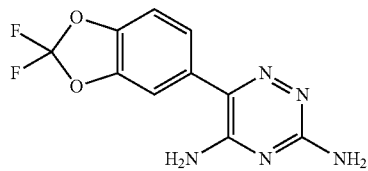 [SMILES: Nc1nnc(-c2ccc3c(c2)OC(F)(F)O3)c(N)n1]

Obtained from 2,2-Difluorobenzodioxole-5-carboxylic acid [Fluorochem] using similar methodology to that employed for example [CEN-115] as a pale yellow solid, melting point 221-222°, tlc (20% methanol+chloroform), $R_f$=0.52

3,5-Diamino-6-[3-(1,1,2,2-tetrafluoroethoxy)phenyl]-1,2,4-triazine [CEN-108]

Obtained from 3-(1,1,2,2,-Tetrafluoroethoxy)benzoic acid [Fluorochem] using similar methodology to that employed for example [CEN-115] as pale cream prisms, melting point 199-200°, tlc (20% methanol+chloroform), $R_f$=0.56

3,5-Diamino-6-[2-(1,1,2,2-tetrafluoroethoxy)phenyl]-1,2,4-triazine [CEN-137]

Obtained from 2-(1,1,2,2,-Tetrafluoroethoxy)benzoic acid [Fluorochem] using similar methodology to that employed for example [CEN-115] as pale cream needles, melting point 158-160°, tlc (20% methanol+chloroform), $R_f$=0.57

3,5-Diamino-6-[2,5-bis(2,2,2-trifluoroethoxy)phenyl]-1,2,4-triazine [CEN-140]

Obtained from 2,5-bis(2,2,2-trifluoroethoxy)benzoic acid [Apollo Scientific Ltd] using similar methodology to that employed for example [CEN-115] as pale cream solid, melting point 99-101°, tlc (20% methanol+chloroform), $R_f$=0.54

3,5-Diamino-6-[2-difluoromethoxy)phenyl]-1,2,4-triazine [CEN-142]

Obtained from 2-(difluoromethoxy)benzoic acid [Apollo Scientific Ltd] using similar methodology to that employed for example [CEN-115] as pale lilac prisms, melting point 154-155°, tlc (10% methanol+chloroform), $R_f$=0.40

3,5-Diamino-6-(3-phenylphenyl)-1,2,4-triazine [CEN-159]

Obtained from 3-biphenylcarboxylic acid [Fluorochem] using similar methodology to that employed for example [CEN-115] as pale cream plates in 75% yield, melting point 215-217° (decomposes), tlc (10% methanol+chloroform), $R_f$=0.34

3,5-Diamino-6-(2-chloro 5 trifluoromethylphenyl)-1,2,4-triazine [CEN-169]

Obtained from 2-chloro-5-trifluoromethylbenzoic acid [JRD Fluorochemicals Ltd] using similar methodology to that employed for example [CEN-115] as pale buff plates in 70% yield, melting point 238-239°, tlc (10% methanol+chloroform), $R_f$=0.37

3,5-Diamino-6-(3-chloro-5-trifluoromethylphenyl)-1,2,4-triazine [CEN-172]

Obtained from 3-chloro-5-trifluoromethylbenzoic acid [JRD Fluorochemicals Ltd] using similar methodology to that employed for example [CEN-115] as pale buff prisms in 82% yield, melting point 249-251°, tlc (10% methanol+chloroform), $R_f$=0.47

3,5-Diamino-6-[3,5 (bis-trifluoromethyl) phenyl]-1,2,4-triazine [CEN-175]

Obtained from 3,5-(bis-trifluoromethyl) benzoic acid [JRD Fluorochemicals Ltd] using similar methodology to that employed for example [CEN-115] as colourless prisms, melting point 350-352° (decompose), tlc (10% methanol+chloroform), $R_f$=0.48

3,5-Diamino-6-(2-chloro-3-trifluoromethylphenyl)-1,2,4-triazine [CEN-176]

Obtained from 2-chloro-3-trifluoromethylbenzoic acid [JRD Fluorochemicals Ltd] using similar methodology to that employed for example [CEN-115] as very pale cream plates in 59% yield, melting point 255-256°, tlc (10% methanol+chloroform), $R_f$=0.34

3,5-Diamino-6-[2-chloro-4-(methylsulphonyl) phenyl]-1,2,4-triazine [CEN-179]

Obtained from 2-chloro-4-(methylsulphonyl) benzoic acid [Fluorochem] using similar methodology to that employed for example [CEN-115] as pale cream prisms in 85% yield, melting point 286-288° (effervesc.), tlc (10% methanol+chloroform), $R_f$=0.32

3,5-Diamino-6-(2,4,6-triisopropylphenyl)-1,2,4-triazine tosylate [CEN-180]

Obtained from 2,4,6-triisopropylbenzoic acid [Alfa Aesar] using similar methodology to that employed for example

[CEN-115] as pale cream prisms in 12.5% yield, melting point decomposes 275-280°, tlc (10% methanol+chloroform), $R_f$=0.48

3,5-Diamino-6-(4-tertbutylphenyl)-1,2,4-triazine [CEN-181]

Obtained from 4-tertbutyllbenzoic acid [Acros Organics] using similar methodology to that employed for example [CEN-115] as bright pale yellow flat needles in 90.5% yield, melting point 275-276°, tlc (10% methanol+chloroform), $R_f$=0.35

3,5-Diamino-6-(4-n-butylphenyl)-1,2,4-triazine [CEN-183]

Obtained from 4-n-butylbenzoic acid [Acros Organics] using similar methodology to that employed for example [CEN-115] as very pale cream prisms in 78.5% yield, melting point 184-186°, tlc (10% methanol+chloroform), $R_f$=0.39

3,5-Diamino-6-(4-fluoro-3-phenoxylphenyl)-1,2,4-triazine tosylate [CEN-184]

Obtained from 4-fluoro-3-phenoxybenzoic acid [Acros Organics] using similar methodology to that employed for example [CEN-115] as pale lemon yellow prisms in 31.5% yield, melting point 226-227°, tlc (10% methanol+chloroform), $R_f$=0.37

Bis-Triazine [CEN-186]

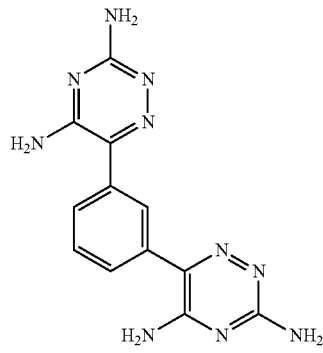 [SMILES: Nc1nnc(-c2cccc(-c3nnc(N)nc3N)c2)c(N)n1]

Obtained from isophthalic acid [Acros Organics] using similar methodology to that employed for example [CEN-115] as a dark cream powder in 92.5% yield, melting point 325-327° (effervesce), tlc (20% methanol+chloroform), $R_f$=0.21

3,5-Diamino-6-(3,5-di-tert-butylphenyl)-1,2,4-triazine [CEN-187]

Obtained from 3,5-di-tert-butylbenzoic acid [Advanced Technology & Industrial Co., Hong Kong] using similar methodology to that employed for example [CEN-115] as colourless needles in 80.6% yield, melting point 278-280°, tlc (10% methanol+chloroform), $R_f$=0.43

3,5-Diamino-6-(3,5-dimethoxyphenyl)-1,2,4-triazine [CEN-192]

Obtained from 3,5-dimethoxybenzoic acid [Sigma Aldrich] using similar methodology to that employed for example [CEN-115] as faintly yellow plates in 98.0% yield, melting point 225-228°, tlc (10% methanol+chloroform), $R_f$=0.45

3,5-Diamino-6-[3,5-bis(2,2,2-trifluoroethoxy)phenyl]-1,2,4-triazine [CEN-193]

Obtained from 3,5-bis-(2,2,2-trifluoroethoxy) benzoic acid [Advanced Technology & Industrial Co., Hong Kong] using similar methodology to that employed for example [CEN-115] as pale cream prisms in 65.3% yield, melting point 185-187°, tlc (10% methanol+chloroform), $R_f$=0.61

3,5-Diamino-6-(3-chloro-2-fluoro-5-trifluoromethylphenyl)-1,2,4-triazine [CEN-197]

Obtained from 3-chloro-2-fluoro-5-trifluoromethylbenzoic acid [JRD Fluorochemicals Ltd] using similar methodology to that employed for example [CEN-115] as an off-white microcrystalline powder in 17% yield, melting point 218-220°, tlc (10% methanol+chloroform), $R_f$=0.35

3,5-Diamino-6-[2,5-bis(trifluoromethyl)phenyl]-1,2,4-triazine tosylate [CEN-198]

Obtained from 3,5-bis-trifluoromethylbenzoic acid [JRD Fluorochemicals Ltd] using similar methodology to that employed for example [CEN-115] as an off-white microcrystalline powder in 16% yield, melting point 218-220°, tlc (10% methanol+chloroform), $R_f$=0.37

3,5-Diamino-6-(2-chloro-3-trifluoromethylphenyl)-1,2,4-triazine [CEN-199]

Obtained from 2-chloro-3-trifluoromethylbenzoic acid [JRD Fluorochemicals Ltd] using similar methodology to that employed for example [CEN-115] as pale buff needles in 17% yield, melting point 218-220°, tlc (10% methanol+chloroform), $R_f$=0.39

3,5-Diamino-6-(5-chloro-2-trifluoromethylphenyl)-1,2,4-triazine [CEN-200]

Obtained from 5-chloro-2-trifluoromethylbenzoic acid [JRD Fluorochemicals Ltd] using similar methodology to that employed for example [CEN-115] as almost colourless prisms in 65% yield, melting point 242-243°, tlc (10% methanol+chloroform), $R_f$=0.41

3,5-Diamino-6-(2,3,4-trifluorophenyl)-1,2,4-triazine [CEN-206]

Obtained from 2,3,4-trifluorobenzoic acid [Fluorochem] using similar methodology to that employed for example [CEN-115] as cream plates in 75% yield, melting point 242-243°, tlc (10% methanol+chloroform), $R_f$=0.33

3,5-Diamino-6-(2-chloro-4,5-difluorophenyl)-1,2,4-triazine [CEN-207]

Obtained from 2-chloro-4,5-difluorobenzoic acid [JRD Fluorochemicals Ltd] using similar methodology to that employed for example [CEN-115] as pale buff plates in 74% yield, melting point 240-242°, tlc (10% methanol+chloroform), $R_f$=0.38

3,5-Diamino-6-(2,3,4,5-tetrafluorophenyl)-1,2,4-triazine [CEN-208]

Obtained from 2,3,4-tetrafluorobenzoic acid [Fluorochem] using similar methodology to that employed for example [CEN-115] as a very pale cream microcrystalline powder in 52.2% yield, melting point 233-235°, tlc (10% methanol+chloroform), $R_f$=0.36

3,5-Diamino-6-(2,3-dichloro-6-trifluoromethylphenyl)-1,2,4-triazine tosylate [CEN-209]

Obtained from 2,3-dichloro-6-trifluoromethylbenzoic acid [JRD Fluorochemicals Ltd] using similar methodology to that employed for example [CEN-115] as very pale greenish yellow prisms in 6.5% yield, melting point: decomposes >265°, tlc (10% methanol+chloroform), $R_f$=0.34

3,5-Diamino-6-(2,3,4,5,6-pentafluorophenyl)-1,2,4-triazine tosylate [CEN-212]

Obtained from 2,3,4,5,6-pentafluorobenzoic acid [Fluorochem] using similar methodology to that employed for example [CEN-115] as a very pale cream microcrystalline powder in 2.5% yield, melting point 355-358°, tlc (10% methanol+chloroform), $R_f$=0.31

3,5-Diamino-6-(2,3,6-trichlorophenyl)-1,2,4-triazine tosylate [CEN-214]

Obtained from 2,3,6-trichlorobenzoic acid [TCI Europe] using similar methodology to that employed for example [CEN-115] as a pale cream powder in 16.5% yield, melting point: decomposes >265°, tlc (10% methanol+chloroform), $R_f$=0.39

Alkoxy-substituted 3,5-Diamino-6-naphthyl-1,2,4-triazine compounds—Procedure [2]

3-Methoxy-2-naphthoyl cyanide

Procedure B

A well stirred mixture [paddle stirrer] of 3-methoxy-2-naphthoyl chloride [prepared from 3-methoxy-2-naphthoic acid by standard procedure] (22.08 g; 0.10 mol), dry toluene (48 cm$^3$), dry acetonitrile (12.0 cm$^3$), copper I cyanide (12.2; 0.136 mol) and Celite (5 g) was heated under reflux until no acid chloride remained (~4.0 hrs). After ~5 minutes, the reaction mixture darkened and then became bright orange and viscous due to complex formation. Additional acetonitrile (15.0 cm$^3$) was added which had the effect of decomposing the orange complex. The dark reaction mixture was cooled to ~80° and diluted with toluene (200 cm$^3$). After stirring for an additional ~30 minutes, the resulting slurry was filtered through a bed of chromatographic silica gel (~2.5 cm) and the pale orange filtrate evaporated in vacuo to constant weight to give the title compound as a bright orange solid.
Yield=19.27 g (91.3%)
Mpt=132-135°

3,5-Diamino-6-[2-(3-methoxynaphthyl)-1,2,4-triazine [CEN-139]

Obtained from the corresponding cyanohydrazone using a similar methodology to that employed for example [CEN-115] as a pale cream solid, melting point 252-254° (decomp.), tlc (15% methanol+chloroform), Rf=0.66
Similarly prepared were:

3,5-Diamino-6-[1-(2-ethoxynaphthyl)-1,2,4-triazine [CEN-110]

Obtained from 2-ethoxy-1-naphthoic acid using similar methodology to that employed for examples [CEN-115+CEN-139] as pale cream prisms, melting point 178-80°, tlc (10% methanol+chloroform), Rf=0.37

3,5-Diamino-6-[2-(3-ethoxynaphthyl)-1,2,4-triazine [CEN-141]

Obtained from 3-ethoxy-2-naphthoic acid using similar methodology to that employed for example [CEN-115+CEN-139] as cream prisms, melting point 212-214°, tlc (15% methanol+chloroform), Rf=0.53

3,5-Diamino-6-[2-(3,7-dimethoxynaphthyl)-1,2,4-triazine [CEN-143]

Obtained from 3,7-dimethoxy-2-naphthoic acid using similar methodology to that employed for example [CEN-115+CEN-139] as dark cream prisms, melting point 274-276° (decomp.), tlc (10% methanol+chloroform), Rf=0.47

3,5-Diamino-6-[2-(1,4-dimethoxynaphthyl)-1,2,4-triazine [CEN-151]

Obtained from 1,4-dimethoxy-2-naphthoic acid using similar methodology to that employed for example [CEN-115+CEN-139] as beige prisms, melting point 142-144° (effervesce., resolidifies), 184-186°, tlc (10% methanol+chloroform), Rf=0.64

3,5-Diamino-6-[1-(2,5-dimethoxynaphthyl)-1,2,4-triazine [CEN-156]

Obtained from 2,5-dimethoxy-1-naphthoic acid using similar methodology to that employed for example [CEN-115+CEN-139] as pale beige prisms, melting point decomposes >275°, tlc (10% methanol+chloroform), Rf=0.60

3,5-Diamino-6-[1-(2,5-dimethoxynaphthyl)-1,2,4-triazine [CEN-157]

Obtained from 2-methoxy-1-naphthoic acid using similar methodology to that employed for example [CEN-115+CEN-139] as pale cream prisms, melting point 255-257° (effervesce.), tlc (10% methanol+chloroform), Rf=0.56

3,5-Diamino-6-[1-(2,5-dimethoxynaphthyl)-1,2,4-triazine [CEN-158]

Obtained from 4,7-dibromo-3-methoxy-2-naphthoic acid using similar methodology to that employed for example [CEN-115+CEN-139] as dark cream prisms, melting point 222-224° (decomp.), tlc (10% methanol+chloroform), Rf=0.48

3,5-Diamino-6-(3-biphenyl)-1,2,4-triazine [CEN-159]

Obtained in from 3-biphenyl carboxylic acid [International Laboratory, USA] using similar methodology to that employed for example [CEN-115] as pale golden yellow plates, melting point 215-217°, tlc (10% methanol+chloroform), $R_f$=0.34

3,5-Diamino-6-Benzyloxyphenyl-1,2,4-triazine compounds—Procedure [3]

Reaction scheme:

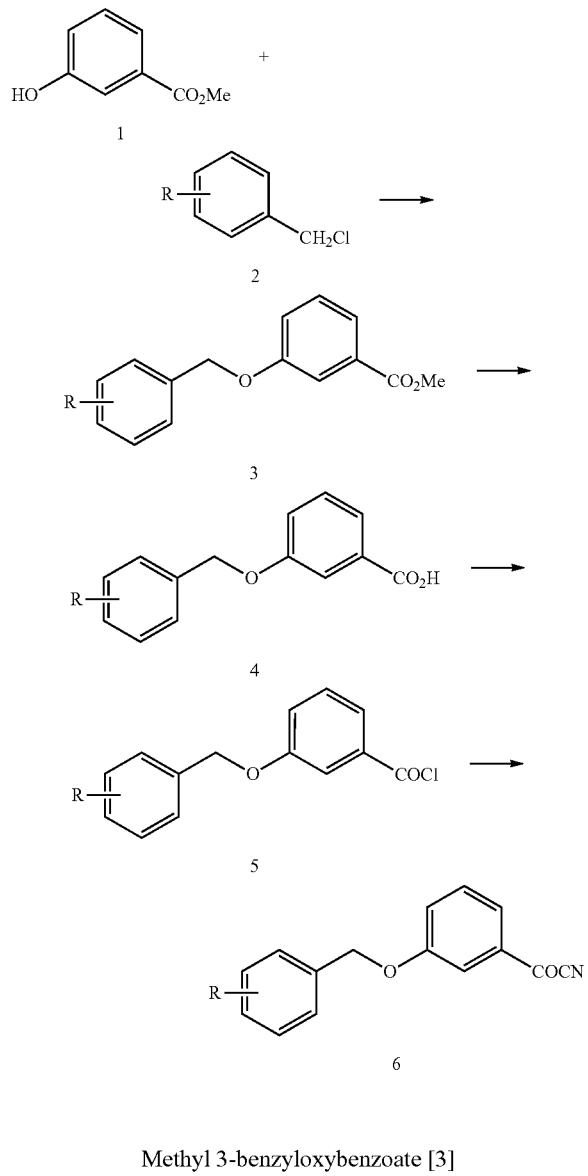

Methyl 3-benzyloxybenzoate [3]

A mixture of methyl 3-hydroxybenzoate [Aldrich] (15.2 g; 0.10 mol), benzyl chloride (12.7 g; 0.10 mol), potassium carbonate (13.8 g; 0.10 mol), potassium iodide (1.0 g) and acetone (150 cm³) was stirred at room temperature until no benzyl chloride remained (~24 hrs).

The mixture was then poured slowly into stirred crushed ice/water (200 cm³) and the precipitated solid filtered off. The product was washed with cold water until neutral and dried in vacuo at 45° to give the title compound as a colourless powder.
Yield=23.9 g (98.8%)
Mpt=77-78°

Tlc [silica gel plate, chloroform], $R_f$=0.72
The product was used directly in next stage.
Similarly prepared were:
Methyl 2-benzyloxybenzoate; yield=96.4%, mpt=46-48°
Methyl 4-benzyloxybenzoate; yield=98.7%, mpt=96-98°
Methyl 3-(2,6-dichlorobenzyloxy)benzoate; yield=94.8%, mpt=87-88°
Methyl 3-(3,4-dichlorobenzyloxy)benzoate; yield=97.8%, mpt=115-117°
Methyl 3-(3,5-bistrifluorobenzyloxy)benzoate; yield=97.9%, mpt=55-57°

3-Benzyloxybenzoic acid [4]

A mixture of methyl 3-benzyloxybenzoate (23.9 g; 0.099 mol), potassium hydroxide (8.42 g; 0.15 mol) and methanol (100 cm³) was stirred at room temperature until a small sample in water gave a clear solution (~18 hrs). The solution was then evaporated to dryness and the colourless solid residue dissolved in water (100 cm³) and the resulting stirred solution was acidified slowly with 50% sulphuric acid (30 cm³). After stirring for ~30 minutes, the crystalline precipitate was filtered, washed with water and dried in vacuo at 40° to give the title compound as a colourless powder.
Yield=22.0 g (97.5%)
Mpt=133-135°
The product was used directly in next stage.
Similarly prepared were:
2-Benzyloxybenzoic acid; yield=98.4%, mpt=77-79°
4-Benzyloxybenzoic acid; yield=97.8%, mpt=187-189°
3-(2,6-Dichlorobenzyloxy)benzoic acid; yield=98.2%, mpt=173-174°
3-(3,4-Dichlorobenzyloxy)benzoic acid; yield=97.5%, mpt=160-162°
3-(3,5-Bistrifluorobenzyloxy)benzoic acid; yield=97.7%, mpt=183-184°

3-Benzyloxybenzoyl chloride [5]

A stirred mixture of 3-benzyloxybenzoic acid (22.0 g; 0.096 mol) and dry dimethylformamide (2 drops) in dry dichloromethane (100 cm³) was treated with oxalyl chloride (19 g; 0.15 mol) which was added in 4 approximately equal portions over ~30 minutes. The mixture was stirred at room temperature until evolution of hydrogen chloride had ceased (~6 hrs). The resulting colourless solution was evaporated in vacuo at 40° to constant weight to give a very pale tan oil that solidified rapidly to give the title compound as off-white needles.
Yield=23.7 g (100.0%)
The product was used directly in next stage.
Similarly prepared were:
2-Benzyloxybenzoyl chloride.
4-Benzyloxybenzoyl chloride
3-(2,6-Dichlorobenzyloxy)benzoyl chloride
3-(3,4-Dichlorobenzyloxy)benzoyl chloride
3-(3,5-Bistrifluorobenzyloxy)benzoyl chloride

3-Benzyloxybenzoyl Cyanide [6]

Procedure A

A well stirred mixture [paddle stirrer] of 3-benzyloxybenzoyl chloride (16.05 g; 0.065 mol), dry toluene (30 cm³), dry acetonitrile (7.5 cm³), copper I cyanide (7.7 g; 0.086 mol) and Celite (4 g) was heated under reflux until no acid chloride remained (~3.5 hrs). The dark reaction mixture was cooled to ~70° and diluted with toluene (125 cm³). After stirring for an additional ~30 minutes, the resulting slurry was filtered through a bed of chromatographic silica gel (~2.5 cm) and the pale tan filtrate evaporated in vacuo to constant weight to give the title compound as a pale tan oil.

Yield=14.83 g (96.3%)

The product was used directly in next stage.

Similarly prepared were:

2-Benzyloxybenzoyl cyanide.

4-Benzyloxybenzoyl cyanide.

3-(2,6-Dichlorobenzyloxy)benzoyl cyanide.

3-(3,4-Dichlorobenzyloxy)benzoyl cyanide, pale yellow solid (95.5%), mpt=122-124°

3-(3,5-Bistrifluorobenzyloxy)benzoyl cyanide.

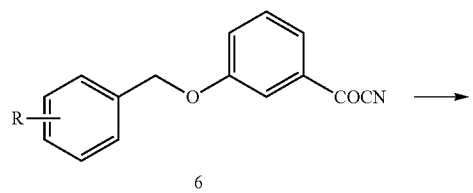

6

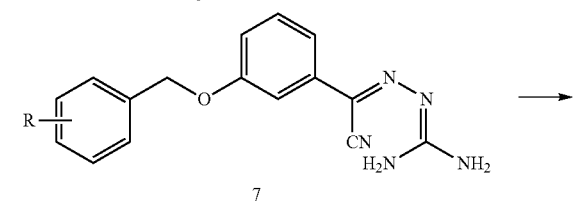

7

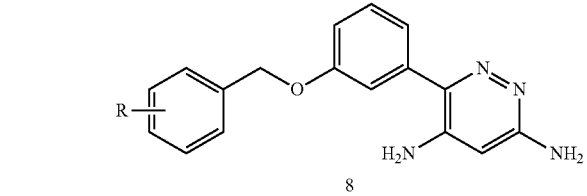

8

Schiffs Base, cyanohydrazone, R=H [7]

Procedure A, Lower Temperature

To a stirred solution of aminoguanidine bismesylate (15.47 g; 0.058 mol) in 99.5% methanesulphonic acid (24 g) at 58-60° was added dropwise a solution of 3-benzyloxybenzoyl cyanide (7.4 g; 0.032 mol) in acetonitrile (20 cm$^3$) over ~25 minutes. The mixture was then stirred at 60° until a sample gave a clear solution in water (~5.5 hrs) and then poured onto crushed ice/water (150 g). The stirred solution was neutralised (pH 8-9) with 48% sodium hydroxide (20.5 cm$^3$) and the precipitated viscous oil extracted into 1:1 butanone ethyl acetate (3×50 cm$^3$). The combined extracts were dried over magnesium sulphate, filtered and evaporated in vacuo to constant weight giving the title compound as a pale tan gum.

Yield=9.1 g (97.8%)

TLC [SiO$_2$ plate, 10% methanol in chloroform], Rf=0.58

The product was used directly in the next stage.

3,5-Diamino-6-(3-Benzyloxyphenyl)-1,2,4-triazine [8] [CEN-123]

A solution of the above cyanohydrazone (9.1 g) in propan-1-ol (50 cm$^3$) was treated with 20% sodium ethoxide solution in ethanol (1.0 cm$^3$) to adjust the pH to 9-10 and the mixture heated under reflux until no starting material remained (2 hrs). The hot tan solution was filtered through a pad of Celite to remove some fine insoluble material and the filtrate stood at 10° for several hours when pale beige prisms were deposited. The product was filtered off, washed with acetone-ether (1:1) and dried at 45° in vacuo giving the title compound as a pale beige solid (7.26 g; 79.8%)

Mpt=284-286°

TLC [SiO2 plate, 10% methanol in chloroform], Rf=0.42

3,5-Diamino-6-(4-Benzyloxyphenyl)-1,2,4-triazine [CEN-131]

Prepared using a similar procedure to that described above from 4-benzyloxybenzoic acid.

The title compound was obtained as a pale cream crystalline solid in 46% yield.

Mpt=205-207°

TLC [SiO2 plate, 10% methanol in chloroform], Rf=0.44

3,5-Diamino-6-[3-(2,4-dichlorobenzyloxyphenyl)]-1, 2,4-triazine [CEN-144]

Prepared using a similar procedure to that described above from 3-(3,4-dichlorobenzyloxy)benzoic acid. The title compound was obtained as pale cream prisms in 77.5% yield, mpt=164-166°, tlc [10% methanol in chloroform], Rf=0.48

3,5-Diamino-6-(2-Benzyloxyphenyl)-1,2,4-triazine [CEN-160]

Prepared using a similar procedure to that described above from 2-benzyloxybenzoic acid.

The title compound was obtained as a pale cream crystalline solid in 65.9% yield.

Mpt=184-186°

TLC [SiO2 plate, 10% methanol in chloroform], Rf=0.46

3,5-Diamino-6-[3-(2,4-trifluoromethylbenzyloxy) phenyl]-1,2,4-triazine [CEN-171]

Prepared using a similar procedure to that described above from 2,4-bistrifluoromethylbenzyloxybenzoic acid. The title compound was obtained as a fine pale cream needles in 60.3% yield, mpt=184-186°, tlc (Silica plate, 10% methanol in chloroform), R$_f$=0.53

3,5-Diamino-6-[3-(2,6-dichlorobenzyloxy)phenyl]-1, 2,4-triazine [CEN-185]

Prepared using a similar procedure to that described above from 2-benzyloxybenzoic acid.

The title compound was obtained as dark cream prisms in 85.1% yield, mpt=190-192°, tlc (Silica plate, 10% methanol in chloroform), R$_f$=0.62

6-Alkyl/Aralkyl-3,5-diamino-1,2,4-triazine compounds-Procedure [4]

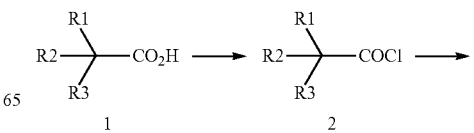

1        2

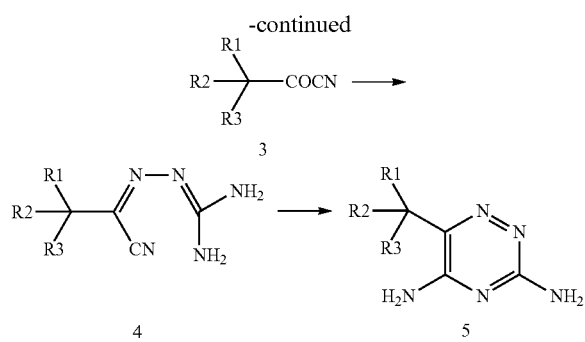

Triphenylacetyl chloride [3; $R_1=R_2=R_3=Ph$]

A stirred mixture of triphenylacetic acid (21.7 g; 0.075 mol) and dry dimethylformamide (2 drops) in dry dichloromethane (100 cm$^3$) was treated with oxalyl chloride (14 g; 0.11 mol) which was added in 4 approximately equal portions over ~25 minutes. The mixture was stirred at 35° until evolution of hydrogen chloride had ceased (~4 hrs). The resulting colourless solution was evaporated in vacuo at 40° to constant weight to give the title compound as a colourless crystalline solid.

Yield=23.24 g (100.0%)
The product was used directly in next stage.
Similarly prepared were:

Triphenylacetyl cyanide [4; $R_1=R_2=R_3=Ph$]

Procedure C, with Potassium Iodide

A well stirred mixture [paddle stirrer] of triphenylacetyl cyanide (23.24 g; 0.075 mol), dry toluene (40 cm$^3$), dry acetonitrile (10 cm$^3$), copper I cyanide (9.20 g; 0.103 mol), Celite (3.5 g) and finely powdered potassium iodide (2 g) was heated under reflux until no acid chloride remained (~18 hrs). The dark reaction mixture was cooled to ~75° and diluted with toluene (150 cm$^3$). After stirring for an additional ~30 minutes, the resulting slurry was filtered through a bed of chromatographic silica gel (~2.5 cm) and the colourless filtrate evaporated in vacuo to constant weight to give the title compound as a colourless solid.

Yield=21.97 g (98.7%)
Mpt=67-69°
The product was used directly in next stage.

Schiffs Base, cyanohydrazone, (4; $R_1=R_2=R_3=Ph$)

Procedure B, Longer Reaction Time

To a stirred solution of aminoguanidine bismesylate (15.00 g; 0.0564 mol) in 99.5% methanesulphonic acid (22.5 g) at 65-70° was added dropwise a solution of Triphenylacetyl cyanide (8.91 g; 0.030 mol) in acetonitrile (25 cm$^3$) over ~25 minutes. The mixture was then stirred at 68° until a sample gave a clear solution in water (~28 hrs) and then poured onto crushed ice/water (150 g) giving a semi-solid colourless precipitate. The mixture was neutralised (pH 8-9) with 48% sodium hydroxide (17.5 cm$^3$) giving the title compound as cream granular solid. The product was filtered off, washed with water and dried in vacuo at 45°.

Yield=8.47 g (80.0%)
Mpt=112-114°
TLC [SiO$_2$ plate, 10% methanol in chloroform], $R_f$=0.68
The product was used directly in the next stage.

3,5-Diamino-6-(triphenylmethy)-1,2,4-triazine [5; $R_1=R_2=R_3=Ph$] [CEN-153]

A solution of the above cyanohydrazone (8.4 g) in propan-1-ol (50 cm$^3$) was treated with 20% sodium ethoxide solution in ethanol (1.5 cm$^3$) to adjust the pH to 9-10 and the mixture heated under reflux until no starting material remained (4.5 hrs). The hot tan solution was filtered through a pad of Celite to remove some fine insoluble material and the filtrate evaporated almost to dryness. The resulting very pale tan oil was dissolved in ether (30 cm$^3$) and the solution stood at 0° when cream prisms were deposited. The product was filtered off, washed with hexane-ether (1:3) and dried at 45° in vacuo giving the title compound as a pale cream solid (4.42 g; 52.6%)

Mpt=124-126°
TLC [SiO2 plate, 10% methanol in chloroform], $R_f$=0.62
Similarly prepared were:

3,5-Diamino-6-(diphenylmethy)-1,2,4-triazine [5; $R_1=H, R_2=R_3=Ph$ [CEN-130]

Obtained from diphenylacetic acid [Aldrich] using similar methodology to that employed for example [CEN-153] as pale cream prisms, melting point 235-237°, tlc (10% methanol+chloroform), $R_f$=0.55

3,5-Diamino-6-(1,1-diphenylethy)-1,2,4-triazine [5; $R_1=M, R_2=R_3=Ph$] [CEN-147]

Obtained from 2,2-diphenylpropionic acid [Aldrich] using similar methodology to that employed for example [CEN-153] as faintly pink prisms, melting point 197-199°, tlc (10% methanol+chloroform), $R_f$=0.43

6-Adamantyl-3,5-diamino-1,2,4-triazine [CEN-083]

Obtained from adamantane carboxylic acid [Aldrich] using similar methodology to that employed for example [CEN-153] as colourless prisms, melting point 304-306°, tlc (20% methanol+chloroform), $R_f$=0.37

3,5-Diamino-6-[1-(4-chlorophenyl)-1-cyclohexyl]-1,2,4-triazine [CEN-145]

Obtained from 1-(4-chlorophenyl)-1-cyclohexanecarboxylic acid [Acros Organics] using similar methodology to that employed for example [CEN-153] as large pale beige needles, melting point 205-207°, tlc (10% methanol+chloroform), $R_f$=0.54

3,5-Diamino-6-[1-(4-chlorophenyl)-1-cyclopenty]-1,2,4-triazine [CEN-148]

Obtained from 1-(4-chlorophenyl)-1-cyclopentanecarboxylic acid [Acros Organics] using similar methodology to that employed for example [CEN-153] as large pale beige needles, melting point 184-186°, tlc (10% methanol+chloroform), $R_f$=0.39

3,5-Diamino-6-[1-(4-chlorophenyl)-1-cyclobuty]-1,2,4-triazine [CEN-152]

Obtained from 1-(4-chlorophenyl)-1-cyclobutanecarboxylic acid [Acros Organics] using similar methodology to

3,5-Diamino-6-[1-(4-chlorophenyl)-1-cyclopropyl]-1,2,4-triazine [CEN-154]

Obtained from 1-(4-chlorophenyl)-1-cyclopropanecarboxylic acid [Acros Organics] using similar methodology to that employed for example [CEN-153] as pale cream prisms, melting point 157-159°, tlc (15% methanol+chloroform), $R_f$=0.55

3,5-Diamino-6-(1-cyclopentyl-1-phenylmethy)-1,2,4-triazine [5; $R_1$=cyclopentyl, $R_2$=Ph, $R_3$=H] tosylate [CEN-163]

Obtained from alpha-phenylcyclopentaneacetic acid [TCI Europe] using similar methodology to that employed for example [CEN-153] in 16.6% yield as pale cream prisms, melting point 268-270°, tlc (10% methanol+chloroform), $R_f$=0.23

3,5-Diamino-6-[1-(6-methoxynaphthalene)ethy)-1,2,4-triazine [5; $R_1$=6-methoxynaphthyl, $R_2$=Me, $R_3$=H] [CEN-165]

Obtained from (+/−)-6-methoxy-alpha-methyl-2-naphthalenecetic acid [TCI Europe] using similar methodology to that employed for example [CEN-153] in 10.6% yield as a pale microcrystalline solid, melting point 210-212°, tlc (10% methanol+chloroform), $R_f$=0.32

3,5-Diamino-6-(9-xanthyl)-1,2,4-triazine [5; $R_1$+$R_2$=xanthyl, $R_3$=H] [CEN-182]

Obtained from xanthene-9-carboxylic acid [TCI Europe] using similar methodology to that employed for example [CEN-153] in 36.8% yield as dark cream prisms, melting point 159-161°, tlc (10% methanol+chloroform), $R_f$=0.42

3,5-Diamino-6-(1-isopropyl-1-phenylmethy)-1,2,4-triazine [5; $R_1$=isopropyl, $R_2$=phenyl, $R_3$=H] tosylate [CEN-201]

Obtained from alpha-isopropylphenylacetic acid [Alfa Aeser] using similar methodology to that employed for example [CEN-153] in 6.6% yield as a pale microcrystalline solid, melting point >300°, tlc (10% methanol+chloroform), $R_f$=0.32

3,5-Diamino-6-[1,1 bis-(4-chlorophenyl)methyl]-1,2,4-triazine [5; $R_1$=$R_2$=4-chlorophenyl, $R_3$=H] tosylate [CEN-213]

Obtained from bis-(4-chlorophenyl)acetic acid [Sigma Aldrich] using similar methodology to that employed for example [CEN-153] as a faintly greenish prisms, melting point>300°, tlc (20% methanol+chloroform), $R_f$=0.65

2-Alkyltriazine Compounds—Procedure [5]

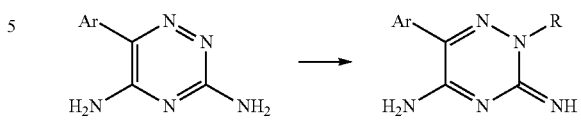

5(3)-Amino-6-(2-phenoxyphenyl)-2,3(2,5)-dihydro-3(5)-imino-2-methyl-1,2,4-triazine [CEN-105]

3,5-Diamino-6-(2-phenoxyphenyl)-1,2,4-triazine (500 mg), methyl methanesulfonate (0.50 g, 4.5 mmol) and methanol (15 cm$^3$) were stirred at 40° for 60 min. The solution was evaporated to dryness and the residue treated with 880 ammonia (2 cm$^3$), After stirring for 20 minutes, the solid was collected by filtration, washed with water and dried. The solid residue was recrystallised from acetone to give the title compound as very pale beige prisms (450 mg), mpt 164-166° (effervesce).

Similarly prepared were:

5(3)-Amino-6-(3-phenoxyphenyl)-2,3(2,5)-dihydro-3(5)-imino-2-methyl-1,2,4-triazine [CEN-106]

The title compound was obtained as very pale yellow prisms (600 mg), mpt 160-161° (decomp.), tlc (20% MeOH in CHCl$_3$), $R_f$=0.31

5(3)-Amino-6-(1-naphthyl)-2,3(2,5)-dihydro-3(5)-imino-2-ethyl-1,2,4-triazine [CEN-077]

The title compound was obtained as light sensitive cream prisms (420 mg), mpt 191-193°, tlc (20% MeOH in CHCl$_3$), $R_f$=0.34

5(3)-Amino-6-(1-naphthyl)-2,3(2,5)-dihydro-3(5)-imino-2-methyl-1,2,4-triazine [CEN-078]

The title compound was obtained as a light sensitive off-white powder (470 mg), mpt 248-250°, tlc (20% MeOH in CHCl$_3$), $R_f$=0.29

5(3)-Amino-6-[3-(2,5-dichlorothienyl)]-2,3(2,5)-dihydro-3(5)-imino-2-methyl-1,2,4-triazine [CEN-080]

The title compound was obtained as pale yellow prisms (490 mg), mpt 286-288°, tlc (10% MeOH in CHCl$_3$), $R_f$=0.21

5(3)-Amino-6-[5-(2,2-difluorobenzodioxolo)]-dihydro-3(5)-imino-2-methyl-1,2,4-triazine [CEN-081]

The title compound was obtained as a pale yellow powder (510 mg), mpt 297-298° (decomp.), tlc (10% MeOH in CHCl$_3$), $R_f$=0.22

5(3)-Amino-6-(2,3,5-trichlorophenyl)-2,3(2,5)-dihydro-3(5)-imino-2-(2,2-difluoroethyl)-1,2,4-triazine [CEN-085]

3,5-Diamino-6-(2,3,5-trichlorophenyl)-1,2,4-triazine (500 mg), 2,2-difluoroethyl methanesulfonate (0.50 g) and methanol (15 cm3) were stirred at 400 for 100 min. The solution was evaporated to dryness and the solid residue treated with 0.880 ammonia solution (3 cm3). After stirring for 10 minutes, the tan residue was collected by filtration and recrystallised from acetone to give the title compound as pale tan needles (145 mg), mpt 168-170 (decomposes).

5(3)-Amino-6-(2,3,-dichlorophenyl)-2,3(2,5)-dihydro-3(5)-imino-2-(2,2,2-trifluoroethyl)-1,2,4-triazine [CEN-067]

A mixture of 3,5-Diamino-6-(2,3,-dichlorophenyl)-1,2,4-triazine (1.28 g), 2,2,2-trifluoroethyl triflate (3.00 g) and dimethylformamide (5 cm$^3$) was stirred at 70° for 1.5 hours. After cooling to room temperature, the solution was treated with 0.880 ammonia solution (3 cm$^3$). After stirring for 24 hours, the tan mixture was treated with water (20 cm$^3$) and the precipitated orange-yellow solid collected by filtration. Recrystallisation from propan-2-ol gave the title compound as a pale yellow solid (470 mg), mpt 179-181° (decomposes). Tlc (DCM+MeOH+aqu.NH$_3$; 3.5:0.5:0.25), R$_f$=0.32

5(3)-Amino-6-(2,3,-dichlorophenyl)-2,3(2,5)-dihydro-3(5)-imino-2-(2-isopropoxy)ethyl-1,2,4-triazine [CEN-091]

A mixture of 3,5-Diamino-6-(2,3,-dichlorophenyl)-1,2,4-triazine (1.00 g), 1-bromo-2-chloroethane (3.00 g) and dimethylformamide (4 cm$^3$) was stirred at 110° for 48 hours. After cooling to room temperature, a pale tan solid crystallised out. This was filtered, washed with ether and dried giving crude 5(3)-amino-6-(2,3,-dichlorophenyl)-2,3(2,5)-dihydro-3(5)-imino-2-(2-chloro)ethyl-1,2,4-triazine hydrobromide (450 mg).

This compound was dissolved in propan-2-ol (10 cm$^3$) and treated with sodium carbonate (1.0 g). After refluxing for 3 hrs, the hot mixture was filtered to remove the inorganic solids. On standing, the title compound crystallised out as a yellow solid. This was collected by filtration. Yield=120 mg, mpt. 198-200° (decomposes). Tlc (DCM+MeOH, 4.5:0.5), R$_f$=0.21
R=Methyl 5(3)-Amino-6-(4-phenoxyphenyl)-2,3(2,5)-dihydro-3(5)-imino-2-methyl-1,2,4-triazine methanesulfonate [CEN-102]

3,5-Diamino-6-(4-phenoxyphenyl)-1,2,4-triazine (500 mg), methyl methanesulfonate (0.50 g, 4.5 mmol) and methanol (15 cm$^3$) were stirred at 40° for 80 min. The solution was evaporated to dryness and the solid residue recrystallised from acetone to give the title compound as colourless needles (525 mg), mpt 174-176°.
Similarly prepared were:

5(3)-Amino-6-phenyl-2,3(2,5)-dihydro-3(5)-imino-2-methyl-1,2,4-triazine methanesulfonate [CEN-051]

The title compound was obtained as a colourless powder (485 mg), mpt 230-232°, tlc (20% MeOH in CHCl$_3$), R$_f$=0.32

5(3)-Amino-6-(2,5-dichlorophenyl)-2,3(2,5)-dihydro-3(5)-imino-2-methyl-1,2,4-triazine methanesulfonate [CEN-053]

The title compound was obtained as a colourless powder (435 mg), mpt 297-298°, tlc (20% MeOH in CHCl$_3$), R$_f$=0.35

5(3)-Amino-6-(3,5-dichlorophenyl)-2,3(2,5)-dihydro-3(5)-imino-2-methyl-1,2,4-triazine methanesulfonate [CEN-059]

The title compound was obtained as a colourless powder (295 mg), mpt 234-236°, tlc (10% MeOH in CHCl$_3$), R$_f$=0.13

5(3)-Amino-6-(2-thienyl)-2,3(2,5)-dihydro-3(5)-imino-2-methyl-1,2,4-triazine methanesulfonate [CEN-061]

The title compound was obtained as very pale yellow plates (505 mg), mpt 201-202°, tlc (10% MeOH in CHCl$_3$), R$_f$=0.16

5(3)-Amino-6-(2-naphthyl)-2,3(2,5)-dihydro-3(5)-imino-2-methyl-1,2,4-triazine methanesulfonate [CEN-076]

The title compound was obtained as a pale yellow solid (590 mg), mpt 243-244°, tlc (20% MeOH in CHCl$_3$), R$_f$=0.32

5(3)-Amino-6-[1-(5,6,7,8-tetrahydronaphthyl)]-2,3(2,5)-dihydro-3(5)-imino-2-methyl-1,2,4-triazine methanesulfonate [CEN-120]

The title compound was obtained as pale cream needles (480 mg), mpt 236-237°, tlc (10% MeOH in CHCl$_3$), R$_f$=0.22

5(3)-Amino-6-[2-(4,5-dibromofuryl)]-2,3(2,5)-dihydro-3(5)-imino-2-methyl-1,2,4-triazine methanesulfonate [CEN-135]

The title compound was obtained as very pale cream prisms (330 mg), mpt 183-185°, tlc (10% MeOH in CHCl$_3$), R$_f$=0.21

5(3)-Amino-6-(2-difluoromethoxyphenyl)-2,3(2,5)-dihydro-3(5)-imino-2-methyl-1,2,4-triazine methanesulfonate [CEN-146]

The title compound was obtained as pale cream prisms (690 mg), mpt 213-215°, tlc (10% MeOH in CHCl$_3$), R$_f$=0.33

5(3)-Amino-6-(1,1-diphenylethyl)-2,3(2,5)-dihydro-3(5)-imino-2-methyl-1,2,4-triazine methanesulfonate [CEN-149]

The title compound was obtained as colourless prisms (505 mg), mpt 240-242°, tlc (10% MeOH in CHCl$_3$), R$_f$=0.29

5(3)-Amino-6-{1-[1-(4-chlorophenyl)]cyclopentyl}-2,3(2,5)-dihydro-3(5)-imino-2-methyl-1,2,4-triazine methanesulfonate [CEN-150]

The title compound was obtained as off-white prisms (410 mg), mpt 272-273°, tlc (10% MeOH in CHCl$_3$), R$_f$=0.28

5(3)-Amino-6-(3-biphenyl)-2,3(2,5)-dihydro-3(5)-imino-2-methyl-1,2,4-triazine methanesulfonate [CEN-161]

The title compound was obtained as very pale cream prisms (76.5% yield), mpt 180-181°, tlc (10% MeOH in CHCl$_3$), R$_f$=0.36

5(3)-Amino-6-(2-chloro-3-trifluoromethyphenyl)-2,3(2,5)-dihydro-3(5)-imino-2-methyl-1,2,4-triazine [CEN-177]

The title compound was obtained as pale yellow solid (81.3% yield), mpt 205-207°, tlc (10% MeOH in CHCl$_3$), R$_f$=0.35

5(3)-Amino-6-{2-(3,4,5-trichloro)thienyl}-2,3(2,5)-dihydro-3(5)-imino-2-methyl-1,2,4-triazine methanesulfonate [CEN-194]

The title compound was obtained as a very pale yellow prisms (85.3%), mpt 192-194° (shrinks at 175-180°), tlc (10% MeOH in CHCl$_3$), R$_f$=0.36

5(3)-Amino-6-(3-chloro-2-fluoro-5-trifluoromethyphenyl)-2,3(2,5)-dihydro-3(5)-imino-2-methyl-1,2,4-triazine mesylate [CEN-202]

The title compound was obtained as pale yellow solid (83.3% yield), mpt 277-279°, tlc (10% MeOH in CHCl$_3$), R$_f$=0.35

5(3)-Amino-6-(2-chloro-4,5-difluoro-5-phenyl)-2,3(2,5)-dihydro-3(5)-imino-2-methyl-1,2,4-triazine mesylate [CEN-204]

The title compound was obtained as colourless prisms (87.6% yield), mpt 319-321°, tlc (10% MeOH in CHCl$_3$), R$_f$=0.37

R=Ethyl

5(3)-Amino-6-phenyl-2,3(2,5)-dihydro-3(5)-imino-2-ethyl-1,2,4-triazine methanesulfonate [CEN-052]

3,5-Diamino-6-phenyl-1,2,4-triazine (500 mg), ethyl methanesulfonate (1.0 g) and ethanol (10 cm$^3$) were stirred at 60° for 4 hours. The solution was evaporated to dryness. Recrystallisation from acetone gave the title compound as colourless needles (425 mg), mpt 240-241°, tlc (20% MeOH in CHCl$_3$), R$_f$=0.37

Similarly prepared were:

5(3)-Amino-6-(2,5-dichlorophenyl)-2,3(2,5)-dihydro-3(5)-imino-2-ethyl-1,2,4-triazine methanesulfonate [CEN-054]

The title compound was obtained as a colourless powder (515 mg), mpt 264-265° (decomp.), tlc (20% MeOH in CHCl$_3$), R$_f$=0.39

5(3)-Amino-6-(2,3,5-trichlorophenyl)-2,3(2,5)-dihydro-3(5)-imino-2-ethyl-1,2,4-triazine methanesulfonate [CEN-055]

The title compound was obtained as a colourless needles (340 mg), mpt 269-271° (decomp.), tlc (20% MeOH in CHCl$_3$), R$_f$=0.29

5(3)-Amino-6-(3,5-dichlorophenyl)-2,3(2,5)-dihydro-3(5)-imino-2-ethyl-1,2,4-triazine methanesulfonate [CEN-060]

The title compound was obtained as a colourless prisms (415 mg), mpt 217-219°, tlc (10% MeOH in CHCl$_3$), R$_f$=0.17

5(3)-Amino-6-(2-thienyl)-2,3(2,5)-dihydro-3(5)-imino-2-ethyl-1,2,4-triazine methanesulfonate [CEN-062]

The title compound was obtained as a very pale yellow powder (390 mg), mpt 194-196°, tlc (10% MeOH in CHCl$_3$), R$_f$=0.19

5(3)-Amino-6-(2-naphthyl)-2,3(2,5)-dihydro-3(5)-imino-2-ethyl-1,2,4-triazine methanesulfonate [CEN-075]

The title compound was obtained as pale yellow prisms (500 mg), mpt 175-177°, tlc (20% MeOH in CHCl$_3$), R$_f$=0.41

5(3)-Amino-6-(3,4,5-trimethoxyphenyl)-2,3(2,5)-dihydro-3(5)-imino-2-ethyl-1,2,4-triazine methanesulfonate [CEN-119]

The title compound was obtained as a pale pink solid (515 mg), mpt 305-306° (decomp.), tlc (10% MeOH in CHCl$_3$), R$_f$=0.23

5(3)-Amino-6-(3-biphenyl)-2,3(2,5)-dihydro-3(5)-imino-2-ethyl-1,2,4-triazine methanesulfonate [CEN-162]

The title compound was obtained as very pale cream prisms (67.2% yield), mpt 224-226°, tlc (10% MeOH in CHCl$_3$), R$_f$=0.38

5(3)-Amino-6-(2-chloro-3-trifluoromethyphenyl)-2,3(2,5)-dihydro-3(5)-imino-2-ethyl-1,2,4-triazine methanesulphonate [CEN-178]

The title compound was obtained as pale yellow solid (76.2% yield), mpt 207-209°, tlc (10% MeOH in CHCl$_3$), R$_f$=0.35

5(3)-Amino-6-(3,5 bis-tert-butylphenyl)-2,3(2,5)-dihydro-3(5)-imino-2-ethyl-1,2,4-triazine methanesulphonate [CEN-189]

The title compound was obtained as colourless needles (55.6% yield), mpt 258-261°, tlc (10% MeOH in CHCl$_3$), R$_f$=0.44

5(3)-Amino-6-{2-(3,4,5-trichloro)thienyl}-2,3(2,5)-dihydro-3(5)-imino-2-ethyl-1,2,4-triazine methanesulfonate [CEN-195]

The title compound was obtained as pale yellow prisms (69.2%), mpt 202-204°, tlc (10% MeOH in CHCl$_3$), R$_f$=0.40

5(3)-Amino-6-(3-chloro-2-fluoro-5-trifluoromethyphenyl)-2,3(2,5)-dihydro-3(5)-imino-2-ethyl-1,2,4-triazine mesylate [CEN-203]

The title compound was obtained as very pale cream prisms (90.7% yield), mpt 277-279°, tlc (10% MeOH in CHCl$_3$), R$_f$=0.39

5(3)-Amino-6-(2-chloro-4,5-difluoro-5-phenyl)-2,3(2,5)-dihydro-3(5)-imino-2-ethyl-1,2,4-triazine mesylate [CEN-205]

The title compound was obtained as very pale cream prisms (83.4% yield), decomposes >245°, tlc (10% MeOH in CHCl$_3$), R$_f$=0.39

5(3)-Amino-6-(3,4,5-trimethoxyphenyl)-2,3(2,5)-dihydro-3(5)-imino-2-methyl-1,2,4-triazine methanesulfonate [CEN-101]

3,5-Diamino-6-(3,4,5-trimethoxyphenyl)-1,2,4-triazine (500 mg), methyl methanesulfonate (0.50 g, 4.5 mmol) methanol (10 cm³) and dimethylformamide (2 cm³) were stirred at 40° for 3 hrs. The mixture was evaporated to dryness and the solid residue recrystallised from propan-2-ol to give the title compound as colourless prisms (615 mg), mpt 258-259°.

6-Adamantyl-5(3)-amino-2,3(2,5)-dihydro-3(5)-imino-2-methyl-1,2,4-triazine methanesulfonate [CEN-100]

6-Adamantyl-3,5-diamino-1,2,4-triazine (500 mg), methyl methanesulfonate (0.50 g, 4.5 mmol) and methanol (10 cm³) were stirred at 40° for 2.5 hrs. The solution was evaporated to dryness and the solid residue recrystallised from acetone to give the title compound as colourless prisms (435 mg), mpt 128-130°.

5(3)-Amino-6-[3,5-(bis-trifluoromethyl)phenyl]-2,3(2,5)-dihydro-3(5)-imino-2-methyl-1,2,4-triazine methanesulfonate [CEN-099]

3,5-Diamino-6-[3,5-(bis-trifluoromethyl)phenyl)-1,2,4-triazine (500 mg), methyl methanesulfonate (0.50 g, 4.5 mmol) and methanol (10 cm³) were stirred at 40° for 1.5 hrs. The mixture was evaporated to dryness and the solid residue recrystallised from acetone to give the title compound as colourless needles (615 mg), mpt 179-181°.

5(3)-Amino-6-(2-phenoxyphenyl)-2,3(2,5)-dihydro-3(5)-imino-2-(1,1,1-trifluoroethyl)-1,2,4-triazine [CEN-098]

3,5-Diamino-6-(2-phenoxyphenyl)-1,2,4-triazine (500 mg), 1-Iodo-2,2,2-trifluoroethane [Fluorochem](1.0 cm³) and ethanol (10 cm³) were stirred at 40° for 124 hrs in a sealed tube. The solution was evaporated to dryness and the residue treated with 880 ammonia (2 cm³). After stirring for 20 minutes, the solid was collected by filtration, washed with water and dried. The solid residue was recrystallised from acetone to give the title compound as colourless prisms (400 mg), mpt 175-177°, (resolidifies), 254-256 (decomposes).

CEN-116

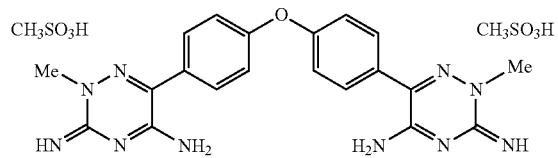

The bis-triazine (500 mg), methyl methanesulfonate (1.00 g, 9.0 mmol) and dimethylformamide (5 cm³) were stirred at 80° until a clear solution was obtained (2.5 hrs). The stirred mixture was cooled to ~45° and flooded with ether (5 cm³) when pale yellow solid was precipitated. The crude product was collected by filtration and recrystallised from propan-2-ol to give the title compound as fine lemon yellow needles (335 mg), mpt 214-216°.

5(3)-Amino-6-(3-chloro-2-fluoro-5-trifluoromethyphenyl)-2,3(2,5)-dihydro-3(5)-imino-2-(2,2,3,3-tetrafluoropropyl)-1,2,4-triazine trifluoromethanesulphonate [CEN-210]

3,5-Diamino-6-(3-chloro-2-fluoro-5-trifluoromethylyphenyl)-1,2,4-triazine (1.4 g), 2,2,3,3-tetrafluoropropyl triflate [Apollo] (1.5 g), butan-2-one (10 cm³) and dimethlformamide (3 drops) were stirred at 80° for 1.5 hrs under nitrogen. The solution was evaporated to dryness and the residue treated with 880 ammonia (2 cm³), After stirring for 20 minutes, the dark cream solid was collected by filtration, washed with water and dried. The crude product was recrystallised from acetone to give the title compound as cream prisms (370 mg), mpt 227-228°, tlc (10% methanol-chloroform), $R_f$=0.44

5(3)-Amino-6-(3-chloro-2-fluoro-5-trifluoromethyphenyl)-2,3(2,5)-dihydro-3(5)-imino-2-(2,2,3,3,3-pentafluoropropyl)-1,2,4-triazine trifluoromethanesuiphonate [CEN-211]

3,5-Diamino-6-(3-chloro-2-fluoro-5-trifluoromethylyphenyl)-1,2,4-triazine (1.4 g), 2,2,3,3,3-pentafluoropropyl triflate [Apollo] (1.5 g), butan-2-one (10 cm³) and dimethlformamide (3 drops) were stirred at 80° for 2.5 hrs under nitrogen. The solution was evaporated to dryness to give a dark cream solid. The crude product was recrystallised from acetone-ether to give the title compound as very pale cream prisms (1.36 g), mpt 221-214° (effervesce.), tlc (10% methanol-chloroform), $R_f$=0.45

3-Amino-5,6-bisaryl 1,2,4-triazine compounds—Procedure [6]

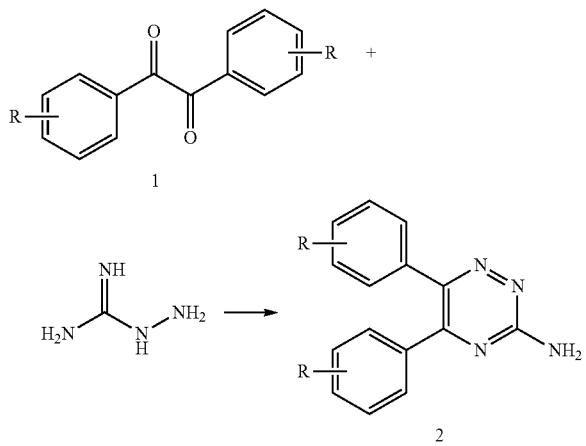

3-Amino-5,6-bis(4-methylphenyl)-1,2,4-triazine (2; R=4-Me) [CEN-126]

A stirred mixture of 4,4'-dimethylbenzil (2.38 g; 0.01 mol), aminoguanidine bismesylate (3.33 g; 0.0125 mol) and ethanol (10 cm3) was heated under reflux until no starting material remained (4 hrs) when a cream solid was deposited. The mixture was evaporated to half volume and basified with 880 ammonia+water (1:1; 4 cm³). On standing, bight yellow prisms were deposited. The product was filtered off, washed with ethanol+water (1:1) and dried in vacuo at 450.

Yield=2.65 g (96.4%)
Mpt=134-136° (lit. 132-134°)
Using the alternative literature* synthesis, the identical product was obtained in 92.3% (mpt=133-135°)

*(Synthesis and anticonvulsant activity of some potent 5,6-bis aryl 1,2,4-triazines B. P. Mallikarjuna et al.; J Zhejiang Univ Sci B. 2007 July; 8(7): 526-532 [http://www.pubmedcentral.nih.gov/articlerender.fcgi?artid=1906601])

3-Amino-5,6-bis(2-chlorophenyl)-1,2,4-triazine (2; R=2-Cl) [CEN-132]

Prepared by reacting 4,4'-dimethoxybenzil with aminoguanidine bismesylate using the above procedure. The title compound was obtained as pale yellow prisms in 91.8%, mpt=240-242°

3-Amino-5,6-bis(4-methoxylphenyl)-1,2,4-triazine (2; R=4-MeO) [CEN-127]

Prepared by reacting 4,4'-dimethoxybenzil with aminoguanidine bismesylate using the above procedure. The title compound was obtained as pale yellow plates in 92.5%, mpt=179-181°

3-Amino-1,2,4-triazine mesylate (4) [CEN-155]

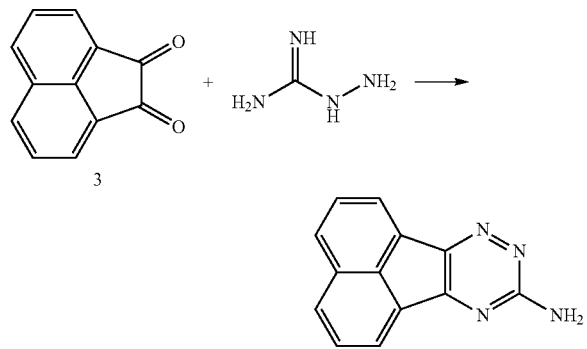

Prepared by reacting acenaphthenequinone (3) with aminoguanidine bismesylate for 24 hrs using the above procedure except that the basification step with ammonia was omitted. The title compound was obtained as bright yellow prisms in 83.2%, mpt=264-266° (froth)

3-Amino-1,2,4-triazine (6) [CEN-128]

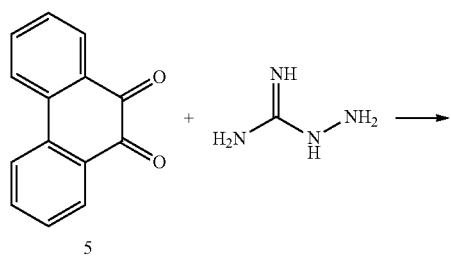

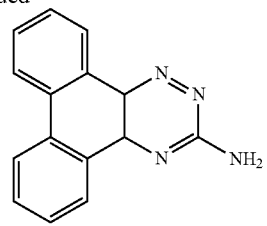

Prepared by reacting 9,10-phenanthrenequinone (5) with aminoguanidine bismesylate using the above procedure. The title compound was obtained as bright yellow prisms in 99.2%, mpt=272-274°

3-Amino-5,6-bis(2-furyl)-1,2,4-triazine [CEN-196]

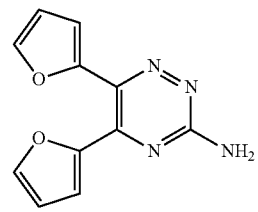 [SMILES: Nc1nnc(-c2ccco2)c(-c2ccco2)n1]

A stirred mixture of 1,2-di(2-furyl)-1,2-dione [Acros Organics] (2.85 g; 0.015 mol), aminoguanidine bismesylate (6.0 g; 0.0225 mol) and ethanol (20 cm3) was heated under reflux until no starting material remained (2 hrs). The mixture was filtered through activated carbon, evaporated to half volume and basified with 880 ammonia+water (1:1; 4 cm$^3$). On standing, brown needles were deposited. The product was filtered off, washed with ethanol+water (1:1) and dried in vacuo at 45°.
Yield=2.50 g (73.1%)
Mpt=211-212° (effervesce.)

3-Amino-2-methyl-5,6-bis(4-methylphenyl)-1,2,4-triazine mesylate (7) [CEN-134]

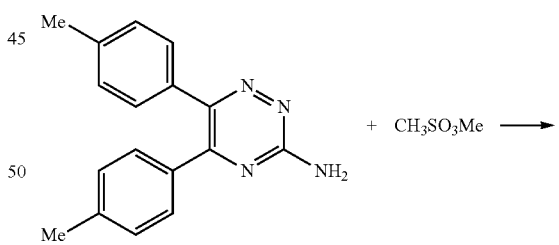

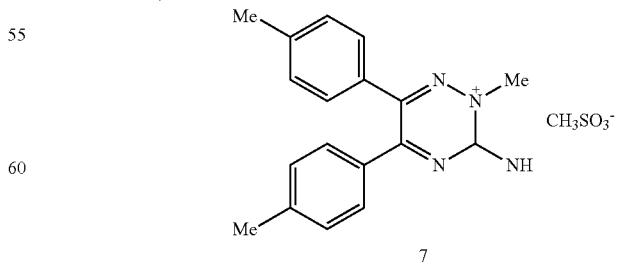

A mixture of 3-amino-5,6-bis(4-methylphenyl)-1,2,4-triazine (500 mg), methyl methanesulphonate (0.5 cm$^3$) and methanol (10 cm³) was stirred at 40° for 24 hours and then evaporated to dryness. The resulting yellow solid was recrystallised from acetone giving the title compound as pale yellow needles, Yield=620 mg (89.2%)
Mpt=205-207°

3-Amino-2-methyl-1,2,4-triazine mesylate (8) [CEN-136]

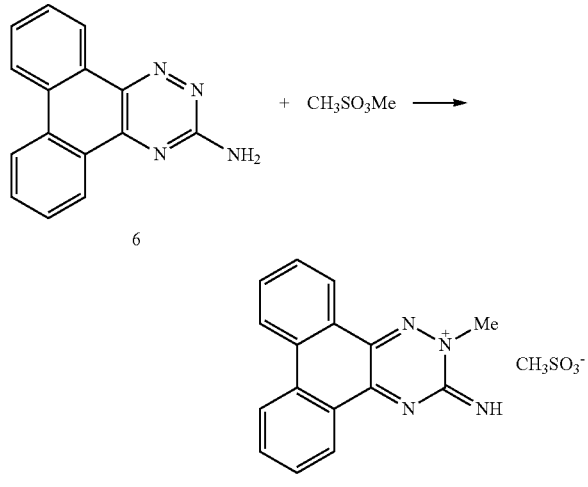

A mixture of the 3-amino-1,2,4-triazine [6] (500 mg), methyl methanesulphonate (0.5 cm³), dimethylformamide (0.5 cm³) and methanol (10 cm³) was stirred at 60° for 30 mins. and the resulting deep yellow solution allowed to stand at room temperature for 24 hrs. The deep yellow plates that were deposited were filtered off washed with acetone-ether (1:1) and dried.

Yield=530 mg (73.3%)
Mpt=277-279°

Pyrimidines

2,4-Diamino-5-(2,3-dichlorophenyl)pyrimidine, [CEN-41]

mp 289-291° C. was prepared by the procedure described in EP— A-0 372 934

4(2)-Amino-5-(2,3-dichlorophenyl)-2,4(2,5)-dihydro-2(4)-imino-1-methylpyrimidine [CEN-42] and 4(2)-Amino-5-(2,3-dichlorophenyl)-2,4(2,5)-dihydro-2(4)-imino-1-methylpyrimidine [CEN-43]

Iodomethane (8 ml) was added to a stirred suspension of 2,4-diamino-5-(2,3-dichlorophenyl)pyrimidine (0.75 g) in methanol (12 ml). The mixture was stirred at 45° C. for 6 h, cooled to room temperature, and diluted with ether (70 ml). A yellow solid deposited and was removed by filtration. This material (0.9 g) was stirred with 0.88 aqueous ammonia (6 ml) and water (10 ml) for 2 h. The white solid was removed by filtration, dried in vacuo and recrystallised from methanol to give 0.25 g of 4(2)-Amino-5-(2,3-dichlorophenyl)-2,4(2,5)-dihydro-2(4)-imino-1-methyl-pyrimidine, mp 226-228° C. (decomp.).

On standing the filtrate deposited 4(2)-Amino-5-(2,3-dichlorophenyl)-2,4(2,5)-dihydro-2(4)-imino-1-methylpyrimidine as pale yellow crystals, which were recrystallised from methanol, mp 289-291° C. Yield 0.24 g.

1H (500 MHz, dmso-$d_6$) 3.52 (3H, s, NCH$_3$), 7.37 (1H, dd, J=7.7, 1.5 Hz, aromatic H), NH), 7.4-7.5 (1H, brpeak, NH, exchang.), 7.48 (1H, t, J=7.7 Hz, aromatic H), 7.76 (1H, dd, J=7.7, 1.5 Hz, aromatic H), 7.95 (1H, s, pyrimidine H), 7.8-8.2 (1H, vbr peak, NH, exchang.), 8.25 (1H, brpeak, NH, exchang.).

2,4-Diamino-5-(2,3,5-trichlorophenyl)pyrimidine [CEN-047]

A known pyrimidine-compound BW 1003C87.

2,4-Diamino-5-(4-chlorophenyl)-6-ethyl-pyrimidine [CEN-048]

A known pyrimidine, commercially available as PYRIMETHAMINE.

Pyrazines

2,6-Diamino-3-(2,3,5-trichlorophenyl)pyrazine [CEN-86]

mp 168-70° C., was prepared by the method described in U.S. Pat. No. 6,255,307

2,6-Diamino-3-(2,3-dichlorophenyl)pyrazine [CEN-87]

mp 150-153° C. (decomp.), was prepared by the method described in U.S. Pat. No. 6,255,307

2,6-Diamino-3-(2-naphthyl)pyrazine [CEN-88]

mp 163-165° C. (decomp.), was prepared by the method described in U.S. Pat. No. 6,255,307

2,6-Diamino-3-(2,2-difluorobenzodioxol-4-yl)pyrazine [CEN-89]

Step 1

2-{[Cyano-(2,2-difluorobenzodioxol-4-yl)methyl]amino}acetamidine hydrobromide

Aminoacetamidine dihydrobromide (1.14 g, 4.9 mmol) was added in portions to a solution of 4-formyl-2,2-difluorobenzodioxole (1.0 g, 5.4 mmol) in methanol (25 ml). Potassium cyanide (0.32 g, 4.9 mmol) was then added in a single portion and the mixture was stirred at room temperature for 4 h and then at 50° C. for 24 h. The mixture was cooled and the solvent removed in vacuo. The residue was slurried in ethyl acetate (25 ml) and water (14 ml) and the tan solid removed by filtration and dried. Yield 0.40 g

Step 2

2,6-Diamino-3-(2,2-difluorobenzodioxol-4-yl)pyrazine

Lithium hydroxide hydrate (0.20 g, 4.8 mmol) was stirred in methanol (20 ml) until dissolution was complete ca. 5 min. 2-{[Cyano-(2,2-difluorobenzodiox-4-yl)methyl]

amino}acetamidine hydrobromide (0.40 g, 1.1 mmol) was then added in portions over 5 min and the solution stirred for 3.5 h at room temperature.

This solution was concentrated in vacuo to 2 ml. Water (40 ml) was added the precipitate removed by filtration and dried. Recrystallisation from toluene-hexane gave the title compound as a light tan solid (0.14 g), mp 135-136° C.

[CEN-90]

A mixture of 2,6-Diamino-3-(2,3,5-trichlorophenyl)pyrazine (180 mg), methyl methanesulphonate (360 mg) and dimethylformamide (2.3 cm³) was stirred at 100° for 15 minutes. After cooling to room temperature, ether (10 cm³) was added producing a deep red oily precipitate. The ethereal layer was decanted off and the residue crystallised from acetone to give a tan hygroscopic solid (180 mg) with an ill-defined melting point.

A. Pyridyl-, Quinolinyl-. Isoquinolinyl-Triazine Compounds

These can be prepared by analogy with the other heteroaryl compounds prepared above 3,5-Diamino-6-[3-(2-chloropyidyl)]-1,2,4-triazine [CEN-164]

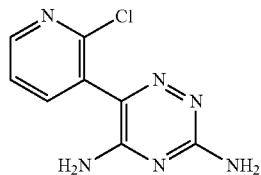 [SMILES: Nc1nnc(-c2cccnc2Cl)c(N)n1]

Obtained from 2-chloronicotinic acid [Sigma Aldrich] using similar methodology to that employed for 3,5-diamino-6-aryl-1,2,4-triazines described above. The product was obtained as a pale cream microcrystalline solid in 93.3% from the hydrazone, melting point 265-266° (effervesce.), tlc (10% methanol+chloroform), $R_f$=0.35

3,5-Diamino-6-[2-(6-chloropyidyl)]-1,2,4-triazine [CEN-166]

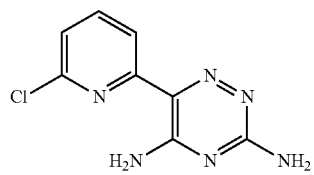 [SMILES: Nc1nnc(-c2cccc(Cl)n2)c(N)n1]

Obtained from 2-chloropicolinic acid [Fluorochem] using similar methodology to that employed for 3,5-diamino-6-aryl-1,2,4-triazines described above. The product was obtained as a fawn prisms in 93.7% from the hydrazone, melting point 300-302°, tlc (10% methanol+chloroform), $R_f$=0.67

3,5-Diamino-6-[3-(2-phenoxypyidyl)]-1,2,4-triazine [CEN-167]

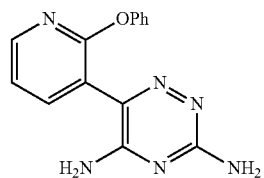 [SMILES: Nc1nnc(-c2cccnc2Oc2ccccc2)c(N)n1]

Obtained from 2-phenoxynicotinic acid [Acros Organics] using similar methodology to that employed for 3,5-diamino-6-aryl-1,2,4-triazines described above. The product was obtained as a colourless crystalline solid in 81.7% from the hydrazone, melting point 223-225° (effervesce.), tlc (10% methanol+chloroform), $R_f$=0.28

3,5-Diamino-6-[3-(5,6-dichloropyidyl)]-1,2,4-triazine [CEN-168]

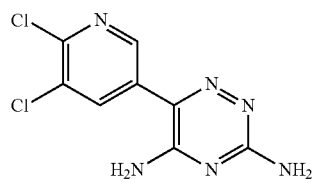 [SMILES: Nc1nnc(-c2cnc(Cl)c(Cl)c2)c(N)n1]

Obtained from 5,6-dichloronicotinic acid [Sigma Aldrich] using similar methodology to that employed for 3,5-diamino-6-aryl-1,2,4-triazines described above. The product was obtained as a pale mustard prisms in 73.8% from the hydrazone, melting point 258-260° (effervesce.), tlc (10% methanol+chloroform), $R_f$=0.28

3,5-Diamino-6-(2-quinolyl)-1,2,4-triazine [CEN-173]

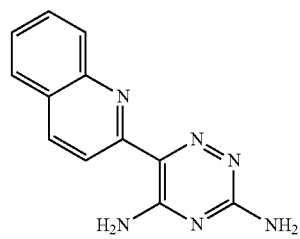 [SMILES: Nc1nnc(-c2ccc3ccccc3n2)c(N)n1]

Obtained from quinaldic acid [AcrosOrganics] using similar methodology to that employed for 3,5-diamino-6-aryl-1,2,4-triazines described above. The product was obtained as a pale mustard microcrystalline solid in 39.0% from the hydrazone, melting point 197-198° (effervesce.), tlc (10% methanol+chloroform), $R_f$=0.42

3,5-Diamino-6-[3-(2,6-dichloropyidyl)]-1,2,4-triazine [CEN-174]

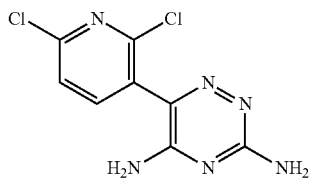 [SMILES: Nc1nnc(-c2ccc(Cl)nc2Cl)c(N)n1]

Obtained from 2,6-dichloronicotinic acid [Fluorochem] using similar methodology to that employed for 3,5-diamino-6-aryl-1,2,4-triazines described above. The product was obtained as a pale mustard prisms in 83.4% from the hydrazone, melting point 255-257° (decomposes), tlc (10% methanol+chloroform), $R_f$=0.38

3,5-Diamino-6-[2-(3,6-dichloropyidyl)]-1,2,4-triazine [CEN-188]

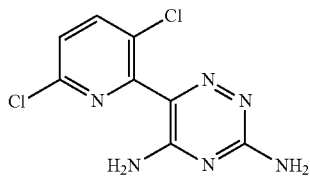 [SMILES: Nc1nnc(-c2nc(Cl)ccc2Cl)c(N)n1]

Obtained from 3,6-dichloropyridine carboxylic acid [Apollo] using similar methodology to that employed for 3,5-diamino-6-aryl-1,2,4-triazines described above. The product was obtained as a pale mustard prisms in 86.5% from the hydrazone, melting point 264-266° (decomposes), tlc (10% methanol+chloroform), $R_f$=0.65

3,5-Diamino-6-[3-(2,6-dichloro-5-fluoropyidyl)]-1,2,4-triazine [CEN-190]

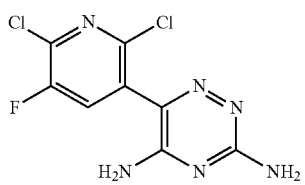 [SMILES: Nc1nnc(-c2cc(F)c(Cl)nc2Cl)c(N)n1]

Obtained from 2,6-dichloro-5-fluoropyridine carboxylic acid [AcrosOrganics] using similar methodology to that employed for 3,5-diamino-6-aryl-1,2,4-triazines described above. The product was obtained as a pale mustard prisms in 45.6% from the hydrazone, melting point 255-257°, tlc (10% methanol+chloroform), $R_f$=0.65

3,5-Diamino-6-[3-(6-chloro-pyridyl)]-1,2,4-triazine [CEN-191]

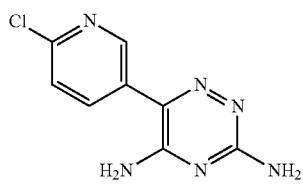 [SMILES: Nc1nnc(-c2ccc(Cl)nc2)c(N)n1]

Obtained from 6-chloro-nicotinic acid [Fluorochem] using similar methodology to that employed for 3,5-diamino-6-aryl-1,2,4-triazines described above. The product was obtained as a pale mustard prisms in 80.2% from the hydrazone, melting point 246-248°, tlc (10% methanol+chloroform), $R_f$=0.23

B. Basic Side-Chain

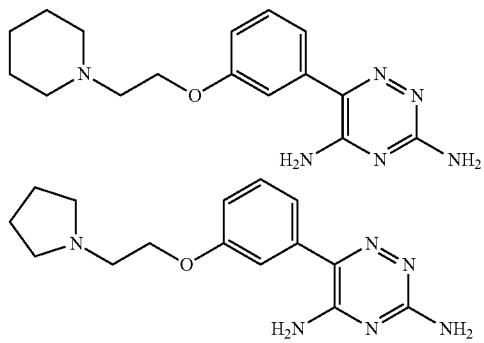

Plus similar targets (2-alkoxy-) and (4-alkoxy-) substitution on the 6-phenyl position

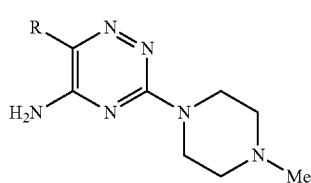

R = selection of groups such as heteroaromatic, diphenylmethyl, and others from the triazine series C. Aliphatic Side-Chain

3,5-Diamino-6-(1-propylbutyl)-1,2,4-triazine tosylate [CEN-170]

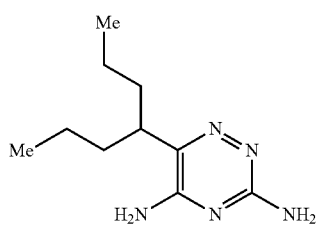 [SMILES: CCCC(CCC)c1nnc(N)nc1N]

Obtained from 2-propylpentanoic acid [Acros Organics] using similar methodology to that employed for 3,5-diamino-6-aryl-1,2,4-triazines described above. The product was obtained as a pale cream microcrystalline solid, melting point 228-230°, tlc (10% methanol+chloroform), $R_f$=0.45

The following compounds are similarly prepared, making reference to procedure (4) above.

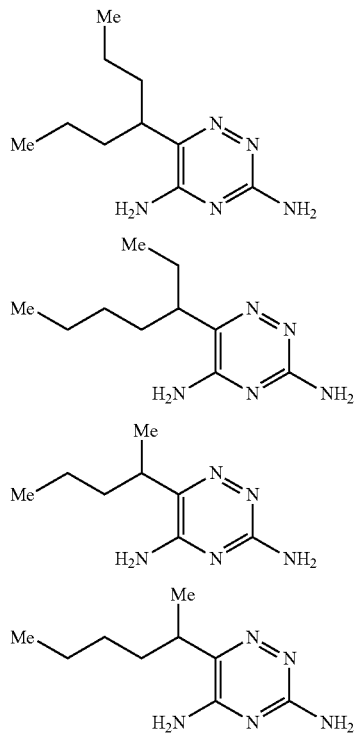

D. Phenoxyalkyl Side Chain 3,5-Diamino-6-{1-(4-chlorophenoxy)-1-methyl}ethyl-1,2,4-triazine tosylate [CEN 215]

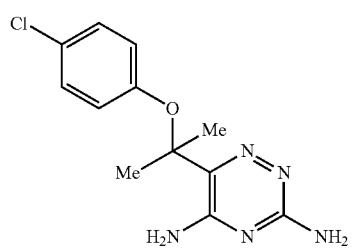 [SMILES: CC(C)(Oc1ccc(Cl)cc1)c1nnc(N)nc1N]

Obtained from 2-(4-chlorophenoxy)-2-methylpropionic acid [Acros Organics] using similar methodology to that employed for 3,5-diamino-6-aryl-1,2,4-triazines described above. The product was obtained as a pale beige microcrystalline solid, melting point 266-268° (decomposes), tlc (10% methanol+chloroform), $R_f$=0.45

The following compounds are similarly prepared, making reference to procedure (4) above.

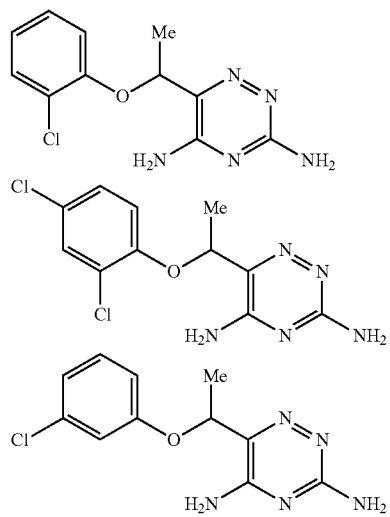

E. Modified 6-Benzyloxyphenyl

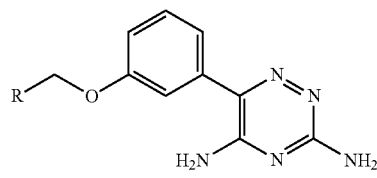

Plus 2- and 4-substitution pattern procedure [3]

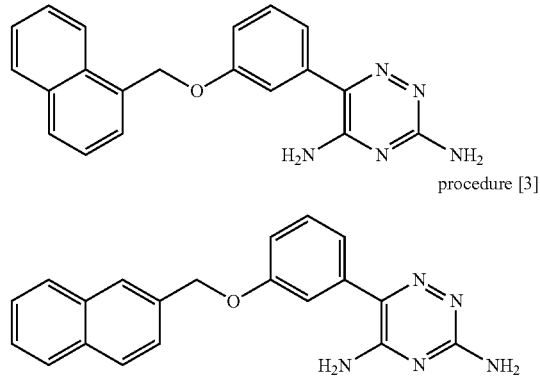

procedure [3]

procedure [3]

procedure [3]

R = 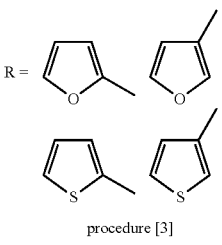

procedure [3]

F. Misc

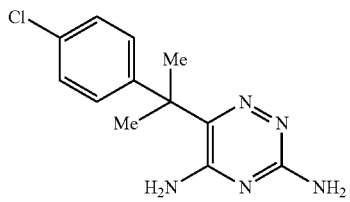

procedure [4]

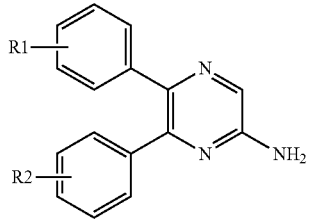

Amino-Pyrazines

R1 = R2 = 2-Cl
= 4-Cl
= 4-OMe
= 4-Me
= H etc

G. Diamino-Pyrazines and Pyrimidine Compounds

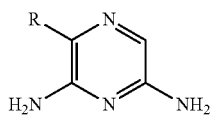

1

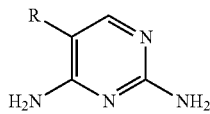

2

R groups can be introduced by analogy with procedures indicated above for correspondingly substituted triazines.

Biological Testing

Compounds of Formula (I) were tested for various activities as follows:

Screening Strategy

The screening strategy is designed to select compounds with appropriate sodium channel blocking activity and low side effect liability. To this end all compounds are processed through the primary sodium channel assay (veratrine-evoked uptake of [$^{14}$C]guanidine into rat forebrain synaptosomes) and $IC_{50}$ values computed from generated concentration-effect curves. In order to complement this data $IC_{50}$'s for selected compounds to inhibit binding of [$^3$H]BTX-B are also measured.

Previous studies have shown that substituted triazines are potential inhibitors of DiHydroFolate Reductase (DHFR) activity (McCullough and Bertino 1971, Cashmore et al, 1975, Booth et al, 1987) and Sapse et al, 1994). Inhibitors of DHFR (such as Methotrexate) have been used for the treatment of various cancers (Suster et al, 1978 and Niculescu-Duvaz et al, 1982) as inhibition of this enzyme interferes with cell growth but because of this effect (on cell growth) inhibitors of DHFR may also be teratogenic (Skalko and Gold, 1974, Feldcamp and Carey, 1993 and Buckley et al, 1997). Should compounds be found which are potent inhibitors of DHFR then such compounds may, themselves, have potential as anti-cancer agents. Several methods are available for measurement of inhibition of DHFR activity and for this study we have examined effects of compounds to inhibit the binding of [$^3$H] methotrexate (Myers et al, 1975 and Rothenberg et al, 1977).

Another common side-effect marker is inhibition of human Ether-a-go-go Related Gene potassium (hERG) potassium channel (Inward rectifying, $I_{Kr}$) activity which can be fatal due to heart failure brought about by development of long QT syndrome. A useful preliminary screen to assess potential to affect this channel is assessed by measurement of inhibition of the binding of [3H]astemizole to cell membranes expressing hERG. Selected compounds are tested for this activity by measurement of inhibition @ 10 µM. Assuming inhibition values lie between 10% and 90% it is possible to compute an extrapolated $IC_{50}$ for each compound.

The above screening cascade identifies compounds with appropriate sodium channel blocking activities that have a low(er) propensity for aforementioned side-effect liabilities. In order to develop these compounds further, some knowledge of their pharmacodynamic properties is required.

Sodium channel blockers, such as Sipatrigine, which both reduces the neurological deficit and infarct volume after middle cerebral artery occlusion in rats (Smith et al, 1997) and phenyloin, (which protect retinal ganglion cell death in an experimental model of glaucoma (Hains and Waxman, 2005) show neuroprotective efficacy in a range of models of nerve degeneration. As failure of oxygen supply compromises both glycolysis and oxidative phosphorylation, ischaemic damage ultimately leads to electrical failure (nerve signalling) and pump failure (restoration of cellular membrane potentials). These failures (of electrical and ion pump activity) are associated with decreased local concentrations of ATP (Astrup et al 1981). Thus the effect of compounds to maintain concentrations of ATP in 0.4 mm slices of rat hippocampus following a severe metabolic insult was used.

Experimental Procedures

Preparation of Rat Forebrain Synaptosomes and Homogenates

Experiments were performed using forebrain (whole brain less cerebellum/medulla) from Male Wistar rats weighing 175-250 g. All efforts were made to reduce the number of animals used and all experiments were carried out in accordance with the UK Animals (Scientific Procedures) Act, 1986 and the European Community Council Directive of 24 Nov. 1986 (86/609/EEC). Following killing of animals by stunning and decapitation, the forebrain (whole brain less cerebellum/medulla) was rapidly dissected and transferred to a weighed tube containing ice-cold 0.25M sucrose.

Synaptosomes (heavy and light mitochondrial fraction containing synaptosomes) were prepared by transferring the forebrain (of known wet weight) to a glass Potter vessel to which 9 volumes ice-cold 0.25M sucrose had been added and homogenising, using a teflon pestle, by 8 'up and down strokes' of a Braun Potter S motor driven homogeniser set to 900 rpm. The resulting homogenate was centrifuged at 1036×g at 4° for 10 min and the supernatant collected. The remaining pellet was resuspended, as above, in fresh ice-cold 0.25M sucrose and the centrifugation step repeated. The supernatant fractions were pooled and centrifuged at 40,000×g (average) at 4° for 15 min and the resulting pellet resuspended in the appropriate assay buffer at a concentration of 20-25 mg wet weight per ml appropriate assay buffer.

Homogenates were prepared by transferring the known weight of forebrain to a cooled tube containing 9 volumes of ice-cold 50 mM pH 7.4 HEPES buffer. The mixture was homogenised @ 4° by 3×5 sec bursts of an Ultra-Turrax™ homogeniser set at maximum speed. The resulting homogenate was centrifuged at 40,000×g (average) at 4° for 15 min and the supernatant discarded. The resulting pellet was resuspended in 9 volumes of fresh ice-cold pH 7.4 buffer (as above), the centrifugation step was repeated and the resulting pellet resuspended in the [$^3$H]BTX-B binding buffer at a concentration of 20-25 mg wet weight per ml assay buffer.

[$^{14}$C] Guanidine Flux and Binding of [$^3$H]BTX-B

Both assays were carried out using 14 ml polypropylene test tubes to which a range of concentrations of the compounds under test were added. Test compounds were dissolved in DMSO and added to assays such that maximum concentration of DMSO did not exceed 2% v/v.

[$^{14}$C]Guanidine Flux:

The [$^{14}$C] guanidinine flux assay was measured using the method of Pauwels P J et al (1986) but carried out @ 30° for 2½ min.

REFERENCES

Pauwels P J, Leysen J E, Laduron P M. [3H]Batrachotoxinin A 20-alpha-benzoate binding to sodium channels in rat brain: characterization and pharmacological significance. Eur J. Pharmacol. 1986 May 27; 124(3):291-8.

Binding of [$^3$H]BTX-B

[$^3$H]BTX-B binding was carried out using the method described by Catterall et al (1981), except that both bovine serum albumin and TTX were omitted from the incubation medium.

REFERENCES

Catterall W A, Morrow C S, Daly J W, Brown G B. Binding of batrachotoxinin A 20-alpha-benzoate to a receptor site associated with sodium channels in synaptic nerve ending particles. J. Bio. Chem. 1981 Sep. 10; 256(17): 8922-7.

Binding of [$^3$H]Methotrexate

All steps were carried out at 4° (or on ice). Freshly dissected rat liver was dissected into 0.25M ice-cold Sucrose and subsequently homogenised (U-turrax) in 50 mM pH 6.0 phosphate buffer (10 ml/g tissue) containing 15 mM Dithiothreitol. The resulting homogenate was centrifuged @ 47,500×g for 20 min and supernatant (filtered through cotton wool to remove fatty lumps) stored @-80° before use (Rothenberg et al).

Inhibition of the binding of [$^3$H]methotrexate to rat liver homogenate supernatant fractions were carried out essentially as described by Arons et al, 1975. Results were calculated, either as IC$_{50}$ values (see below) derived from concentration-effect curves or as percentage inhibition values determined by comparison with control and cold Methotrexate (10 μM final concentration) binding values.

REFERENCES

Elliot Arons, Sheldon P. Rothenberg, Maria da Costa, Craig Fischer and M. Perwaiz Iqbal; Cancer Research 35, Aug. 1, 1975, 2033-2038, Computation of IC$_{50}$ Values Data are presented as mean±sem of number of experiments indicated in brackets. IC$_{50}$ values were obtained from radioligand displacement or guanidine flux inhibition curves by plotting log$_{10}$ concentration vs bound ligand/guanidine uptake according the equation:—

$$y = R\text{min} + Rsp/\{1+\exp[-n(x-C)]\}$$

where
y=bound (dpm)
x=log$_{10}$ compound concentration
Rmin=lower asymptote (i.e. 100% inhibition)
Rsp=upper asymptote-Rmin (i.e. specific binding)
n=slope (log$_e$)
and
C=IC$_{50}$ (i.e. concentration required to inhibit 50% of specific binding Hippocampal Slice Assay Neuroprotective efficacy was measured in 0.4 mm slices of rat hippocampus using the method described by Fowler and Li (1998)[1] except that Iodoacetate (400 μM)[2] was used as the metabolic insult. Compounds (usually 30 μM) were always directly compared with tetrodotoxin (1 μM)[3] for their ability to maintain slice concentrations of ATP following inhibition of glycolysis.

1. Fowler J C, Li Y. Contributions of Na$^+$ flux and the anoxic depolarization to adenosine 5'-triphosphate levels in hypoxic/hypoglycemic rat hippocampal slices. Neuroscience 1998, 83, 717-722.
2. Reiner P B, Laycock A G, Doll C J. A pharmacological model of ischemia in the hippocampal slice. Neurosci Lett 1990; 119:175-8
3. Boening J A, Kass I S, Cottrell J E, Chambers G. The effect of blocking sodium influx on anoxic damage in the rat hippocampal slice. Neuroscience. 1989. vol 33 (2), 263-268.

REFERENCES

Measurement of ATP and Protein

Individual slices were disrupted by ultra-sonication and the resulting homogenates centrifuged @ 10000×g for 5 min @ 4°. The supernatant was decanted into a fresh tube and any remaining supernatant removed by vacuum aspiration. The pellet was resuspended in 0.5 ml 0.1M KOH by ultra-sonication and the resulting suspensions warmed with gentle agitation @ 37° for 30 minutes.

Concentrations of ATP were measured in 6 μl of supernatant by mixing with Luciferase reagent (ATPLite from Perkin Elmer) and measuring subsequent luminescence in a 96-well plate Counter.

Protein concentration was measured using BCA™ protein assay (Pierce) withBovine Serum albumin as reference standard.

ATP concentrations were expressed as nmoles/mg protein and neuroprotective indices (% protection) calculated by direct comparison with the effect of 1 μM TTX.

hERG:

Compounds were sent to MDS Pharma for measurement of their inhibition @ 10 μM concentration of the binding of [$^3$H]astemizole to HEK-293 cells expressing human recombinant hERG. Making the assumption that binding slopes would be 1.0 IC$_{50}$ values could be calculated (see above) for compounds exhibiting between 5% and 95% inhibition of binding.

L-Type Calcium Channels

Compounds were sent to MDS Pharma for measurement of their inhibition @ 10 μM concentration of the binding of [$^3$H]nitrendipine to rat cerebral cortex membranes. Making the assumption that binding slopes would be 1.0 IC$_{50}$ values could be calculated (see above) for compounds exhibiting between 5% and 95% inhibition of binding.

Rat Microsome Stability

Compounds were sent to BioFocus for measurement of their stability @ 1 μM concentration following incubation with rat liver microsomes for 40 minutes @ 37°.

Results

Data from the various testing procedures is set out in the Table below:

| CEN nr | [$^{14}$C]guanidine flux Mean IC$_{50}$ (μM) | [$^3$H]mtx binding IC$_{50}$ (μM) (% inhibition @ 125 μM) | hERG % inhibition @ 10 μM | hERG IC$_{50}$ (μM) (extrapolated from 10 μM inh'n) | L-type Ca$^{2+}$ % inhibition @ 10 μM | L-type Ca$^{2+}$ IC$_{50}$ (μM) (extrapolated from 10 μM inh'n) | Microsome stability % metabolised (40 min incubation 37°) |
|---|---|---|---|---|---|---|---|
| 1 (Ltg) | 219.2 | 631(17 ± 2(4)) 11** 68* (***) | 1 | 989 | 17 | 48.8 | 0.5 |
| 41 | 60.3 | 76 | −3 | >200 | — | — | — |
| 42 | 616.6 | 32 | — | — | — | — | — |
| 43 | 631.0 | 20 | — | — | — | — | — |
| 47 | 13.2 | — | 22 | 35 | — | — | — |
| 48 | 5.8 | — | 18 | 46 | −1 | >>190 | — |
| 57 | >2000 | 44 | — | — | — | — | — |
| 61 | 676.1 | 87 | — | — | — | — | — |
| 62 | 141.3 | 46 | −13 | >200 | — | — | — |
| 64 | >2000 | 52 | — | — | — | — | — |
| 67 | 4.3 | 11 | 15 | 57 | −16 | >>190 | 0.5 |
| 68 | 794.3 | 101 | — | — | — | — | — |
| 69 | 776.2 | 66 | — | — | — | — | — |
| 70 | 1513.6 | 66 | — | — | — | — | — |
| 71 | 512.9 | 54 | — | — | — | — | — |
| 72 | 131.8 | 101 | — | — | — | — | — |
| 73 | 81.2 | 5 | 3 | >200 | 8 | 114.9 | 62.5 |
| 74 | 295.1 | 99 | — | — | — | — | — |
| 75 | 49.0 | 5 | 78 | 3 | — | — | — |
| 76 | 77.6 | 6 | 74 | 4 | — | — | — |
| 77 | 14.5 | −1 | 36 | 18 | — | — | — |
| 78 | 102.3 | 9 | 24 | 32 | — | — | — |
| 79 | 208.9 | −1 | 3 | >200 | 17 | 48.8 | 0.0 |
| 80 | 123.0 | −1 | 14 | 61 | — | — | — |
| 81 | 251.1 | −2 | 17 | 49 | — | — | — |
| 82 | >1000 | −8 | — | — | — | — | — |
| 83 | 40.8 | −5 | 16 | 52 | — | — | — |
| 84 | 43.7 | −4 | 9 | 101 | 7 | 132.8 | 33.0 |
| 85 | 3.6 | −5 | 39 | 16 | −15 | >>190 | — |
| 86 | 14.1 | −5 | 1 | >200 | 9 | 101.1 | — |
| 87 | 288.4 | −5 | 3 | >200 | 7 | 132.8 | — |
| 88 | 190.5 | 82 | — | — | — | — | — |
| 89 | 724.4 | 101 | — | — | — | — | — |
| 90 | 97.7 | 53 | — | — | — | — | — |
| 91 | 371.5 | 94 | — | — | — | — | — |
| 92 | 144.5 | 15 | 4 | >200 | 3 | >190 | 0.0 |
| 93 | 63.1 | 4 | 35 | 19 | — | — | — |
| 94 | 398.1 | −2 | — | — | — | — | — |
| 95 | >>1000 | 6 | — | — | — | — | — |
| 96 | 109.6 | 105 | — | — | — | — | — |
| 97 | 363.1 | 101 | — | — | — | — | — |
| 98 | 8.9 | 41 | 18 | 46 | −18 | >>190 | 6.0 |
| 99 | 134.9 | −1 | 23 | 34 | — | — | 0.0 |
| 100 | 77.6 | 10 | 30 | 23 | — | — | — |
| 101 | >>1000 | 65 | — | — | — | — | — |
| 102 | 58.9 | 25 | — | — | — | — | — |
| 103 | >>1000 | 47 | — | — | — | — | — |
| 104 | >>1000 | 23 | — | — | — | — | — |
| 105 | 100.0 | 86 | 35 | 19 | — | — | — |
| 106 | 26.9 | 43 | — | — | — | — | — |
| 107 | 1174.9 | 48 | — | — | — | — | — |
| 108 | 812.8 | 81 | — | — | — | — | — |
| 109 | >>1000 | 80 | — | — | — | — | — |
| 110 | 134.9 | −23 | −12 | >200 | — | — | 61.5 |
| 111 | 912.0 | 97 | — | — | — | — | — |
| 112 | 1000.0 | 84 | — | — | — | — | — |
| 113 | 1995.3 | 65 | — | — | — | — | — |
| 114 | 173.8 | 46 | — | — | — | — | — |
| 115 | >>1000 | 61 | — | — | — | — | — |
| 116 | 955.0 | 70 | — | — | — | — | — |
| 117 | >>1000 | 79 | — | — | — | — | — |
| 118 | 1148.2 | −7 | — | — | — | — | — |
| 119 | 1949.8 | 52 | — | — | — | — | — |
| 120 | 195.0 | 18 | 6 | 157 | — | — | — |
| 121 | >>1000 | 92 | — | — | — | — | — |
| 122 | >>1000 | 86 | — | — | — | — | — |
| 123 | 41.7 | 86 | — | — | — | — | — |
| 124 | 871.0 | 90 | — | — | — | — | — |
| 125 | 7585.8 | 6 | — | — | — | — | — |
| 126 | 58.9 | −12 | 79 | 3 | — | — | — |
| 127 | 85.1 | −24 | 2 | >200 | — | — | — |
| 128 | 251.2 | 0 | 16 | 53 | — | — | — |
| 129 | 190.5 | −3 | 7 | 133 | — | — | — |
| 130 | 20.4 | 2 | −2 | >200 | — | — | — |

-continued

| CEN nr | [$^{14}$C]guanidine flux Mean IC$_{50}$ (μM) | [$^3$H]mtx binding IC$_{50}$ (μM) (% inhibition @ 125 μM) | hERG % inhibition @ 10 μM | hERG IC$_{50}$ (μM) (extrapolated from 10 μM inh'n) | L-type Ca$^{2+}$ % inhibition @ 10 μM | L-type Ca$^{2+}$ IC$_{50}$ (μM) (extrapolated from 10 μM inh'n) | Microsome stability % metabolised (40 min incubation 37°) |
|---|---|---|---|---|---|---|---|
| 131 | 288.4 | 94 | — | — | — | — | — |
| 132 | 69.2 | 4 | — | — | — | — | — |
| 133 | >>2000 | 17 | — | — | — | — | — |
| 134 | 4.9 | 6 | — | — | — | — | — |
| 135 | 43.7 | 89 | — | — | — | — | — |
| 136 | 229.1 | 27 | — | — | — | — | — |
| 137 | >>2000 | 23 | — | — | — | — | — |
| 138 | >>2000 | 67 | — | — | — | — | — |
| 139 | 288.4 | 46 | — | — | — | — | — |
| 140 | 229.1 | 3 | — | — | — | — | — |
| 141 | 288.0 | 30 | — | — | — | — | — |
| 142 | >>2000 | 12 | — | — | — | — | — |
| 143 | >>2000 | 27 | — | — | — | — | — |
| 144 | 57.5 | 96 | — | — | — | — | — |
| 145 | 9.6 | 39 | — | — | — | — | — |
| 146 | 871.0 | 3 | — | — | — | — | — |
| 147 | 60.3 | 4 | — | — | — | — | — |
| 148 | 20.4 | 38 | — | — | — | — | — |
| 149 | 23.4 | 4 | — | — | — | — | — |
| 150 | 16.2 | 27 | — | — | — | — | — |
| 151 | 67.6 | 76 | — | — | — | — | — |
| 152 | 478.6 | 1 | — | — | — | — | — |
| 153 | 50.1 | 2 | — | — | — | — | — |
| 154 | 162.2 | 13 | — | — | — | — | — |
| 155 | 34 | −6 | 22 | 35 | — | — | — |
| 156 | 246 | 32 | — | — | — | — | — |
| 157 | 204 | −1 | 6 | 157 | — | — | — |
| 158 | >1000 | −1 | — | — | — | — | — |
| 159 | 44 | 97 | — | — | — | — | — |
| 160 | 295 | −11 | 0 | >200 | — | — | — |
| 161 | 16 | −7 | 88 | 1 | — | — | — |
| 162 | 12 | 57 | — | — | — | — | — |
| 163 | 8 | 13 | 11 | 81 | — | — | — |
| 164 | 692 | 0 | — | — | — | — | — |
| 165 | 372 | −4 | 23 | 34 | — | — | — |
| 166 | 1175 | 88 | — | — | — | — | — |
| 167 | >>2000 | −2 | — | — | — | — | — |
| 168 | 1000 | 95 | — | — | — | — | — |
| 169 | 347 | 95 | — | — | — | — | — |
| 170 | 263 | 29 | — | — | — | — | — |
| 171 | 2 | 91 | — | — | — | — | — |
| 172 | 234 | 100 | — | — | — | — | — |
| 173 | 159 | 34 | — | — | — | — | — |
| 174 | 589 | 4 | 9 | 101 | — | — | — |
| 175 | >>2000 | −4 | — | — | — | — | — |
| 176 | 309 | 55 | — | — | — | — | — |
| 177 | 14 | 16 | 22 | 35 | — | — | — |
| 178 | 28 | 27 | — | — | — | — | — |
| 179 | >>2000 | −1 | — | — | — | — | — |
| 180 | >>2000 | −2 | — | — | — | — | — |
| 181 | 74 | 101 | — | — | — | — | — |
| 182 | 214 | 6 | 10 | 90 | — | — | — |
| 183 | 39 | 106 | — | — | — | — | — |
| 184 | 34 | 104 | — | — | — | — | — |
| 185 | 3 | 90 | — | — | — | — | — |
| 186 | >>2000 | 83 | — | — | — | — | — |
| 187 | 447 | 99 | — | — | — | — | — |
| 188 | 2570 | 76 | — | — | — | — | — |
| 189 | 468 | 2 | 10 | 90 | — | — | — |
| 190 | 813 | 6 | — | — | — | — | — |
| 191 | 1950 | 31 | — | — | — | — | — |
| 192 | >>2000 | 91* (***) | — | — | — | — | — |
| 193 | 135 | 99* (***) | — | — | — | — | — |
| 194 | 9 | −6* (***) | — | — | — | — | — |
| 195 | 4 | −2* (***) | — | — | — | — | — |

-continued

| CEN nr | [$^{14}$C]guanidine flux Mean IC$_{50}$ (μM) | [$^3$H]mtx binding IC$_{50}$ (μM) (% inhibition @ 125 μM) | hERG % inhibition @ 10 μM | hERG IC$_{50}$ (μM) (extrapolated from 10 μM inh'n) | L-type Ca$^{2+}$ % inhibition @ 10 μM | L-type Ca$^{2+}$ IC$_{50}$ (μM) (extrapolated from 10 μM inh'n) | Microsome stability % metabolised (40 min incubation 37°) |
|---|---|---|---|---|---|---|---|
| 196 | 912 | 41* (***) | — | — | — | — | — |
| 197 | 91 | 95* (***) | — | — | — | — | — |

*99 μM
**198 μM
(***) uses fresh batch of supernatant
Inhibition of binding of [3H]batrachotoxinin binding to rat (wistar) brain
Data are presented as % inhibition @ 10 μM and extrapolated IC$_{50}$'s (which assumes hill slope = 1).
Compounds which give <5% inhibition are ascribed IC$_{50}$'s of >200 μM
Compounds which give >95% inhibition are ascribed IC$_{50}$'s of <0.5 μM Inhibition of Binding of [3H]BTX-B

| Compound | % inhibition (@ 10 μM) | Extrapolated IC50 (μM) |
|---|---|---|
| CEN-1 | −28 | >200 |
| CEN-198 | 23 | 34 |
| CEN-199 | 29 | 25 |
| CEN-200 | 14 | 61 |
| CEN-201 | 3 | >200 |
| CEN-202 | 90 | 1 |
| CEN-203 | 102 | <0.5 |
| CEN-204 | 52 | 9 |
| CEN-205 | 79 | 3 |
| CEN-206 | 24 | 32 |
| CEN-207 | 30 | 23 |
| CEN-208 | 31 | 22 |
| CEN-209 | 36 | 18 |
| CEN-210 | 43 | 13 |
| CEN-211 | 106 | <0.5 |
| CEN-212 | 0 | >200 |
| CEN-213 | −2 | >200 |
| CEN-214 | 10 | 90 |
| CEN-215 | 22 | 35 |

Summary of [3H]Batrachotoxinin Binding Method-279510
Sodium Channel, Site 2
Source: Wistar Rat brain
Ligand: 5 nM [.H] Batrachotoxin
Vehicle: 1% DMSO
Incubation Time/Temp: 60 minutes @ 37.0
Incubation Buffer: 50 mM HEPES, 50 mM Tris-HCl, pH7.4, 130 mM Choline Chloride,
    5.4 mM KCl, 0.8 mM MgCl., 5.5 mM Glucose, 40 μg/ml LqTx
K$_D$: 0.052 μM*
Non-Specific Ligand: 100 μM Veratridine
Bmax: 0.7 pmole/mg Protein *
Specific binding: 77%
Quantitation Method Radioligand Binding
Significance Criteria: >/=50% of max stimulation or Inhibition
Hippocampal Slice Data

| Standard Compound | Conc'n (μM) | % protection (v 1 μM TTX) (mean ± sem) |
|---|---|---|
| TTX | 1 | 100 |
| Lamotrigine | 30 | 41 ± 5 (3) |
| [CEN-001] Sipatrigine | 30 | 58 ± 6 (7) |
| DPH | 30 | 48 (no. of expt's) |

| Compound | Conc'n (μM) | % protection (v 1 μM TTX) (mean ± sem) |
|---|---|---|
| CEN-47 | 30 | 98 |
| CEN-67 | 30 | 3 |
| CEN-86 | 30 | 98 |
| CEN-92 | 30 | 32 |
| CEN-98 | 30 | 11 |
| CEN-130 | 30 | 39 |
| CEN-140 | 30 | −11 |
| CEN-152 | 30 | −10 |
| CEN-160 | 30 | 0 |
| CEN-163 | 30 | 56 |

The screening data obtained in respect of representative compounds of the invention points to the suitability of compounds of general formula (I)) for treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motorneurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

What is claimed is:

1. A method of treating a disorder comprising administering to a subject in need thereof a compound of general formula (I), or a salt or solvate thereof,

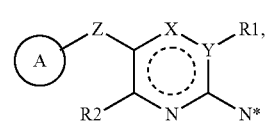

(I)

in which:
X and Y are each N;
Z is a single bond or an optionally substituted linking group;
R1 is hydrogen, or a substituent group, or the Y nitrogen is unsubstituted;

R2 is amino or a substituent group;
N* is amino when R1 is hydrogen or =NH when R1 is a substituent group; or
N* is a group NRaRb where Ra and Rb are independently H or an alkyl group; or
N* is an optionally substituted piperazinyl ring; and
A is a sulphur containing heterocycle substituted with halogen, alkyl or alkoxy;
wherein the disorder is a neurodegenerative disorder, motor neurone disease, Alzheimer's disease, Parkinson's disease, bipolar disorder, a mood disorder, an anxiety disorder, a cognitive disorder, or schizophrenia.

2. The method according to claim 1, wherein the sulphur containing heterocycle is substituted with 1, 2, or 3 chlorine or bromine atoms.

3. The method according to claim 1, wherein the compound is selected from the group consisting of:
3,5-Diamino-6-[3-(2,5-dichlorothienyl)]-1,2,4-triazine [CEN-071];
3,5-Diamino-6-[2-(3,4,5-trichlorothienyl)]-1,2,4-triazine [CEN-079];
5(3)-Amino-6-[3-(2,5-dichlorothienyl)]-2,3(2,5)-dihydro-3(5)-imino-2-methyl-1,2, 4-triazine [CEN-080];
5(3)-Amino-6-{2-(3,4,5-trichloro)thienyl}-2,3(2,5)-dihydro-3(5)-imino-2-methyl-1,2, 4-triazine [CEN-194];
5(3)-Amino-6-{2-(3,4,5-trichloro)thienyl}-2,3(2,5)-dihydro-3(5)-imino-2-ethyl-1,2,4-triazine [CEN-195];
3,5-Diamino-6-[2-(4,5-dibromothienyl)]-1,2,4-triazine [CEN-122];
3,5-Diamino-6-[2-(5-bromothienyl)]-1,2,4-triazine [CEN-124];
3,5-Diamino-6-[2-(3-bromothienyl)]-1,2,4-triazine [CEN-125];
3,5-Diamino-6-[2-(5-chlorothienyl)]-1,2,4-triazine [CEN-138]; and
and
3,5-Diamino-6-[2-(3-chlorobenzo[b]thiophenyl)]-1,2,4-triazine [CEN-114].

4. The method according to claim 1, wherein the compound is 3, 5-Diamino-6-[2-(3,4,5-trichlorothienyl)]-1,2,4-triazine [CEN-079].

5. The method of claim 1, wherein the disorder is motor neurone disease.

6. The method according to claim 3, wherein the disorder is motor neurone disease.

7. A compound of general formula (I), or a salt or solvate thereof,

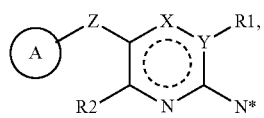

(I)

in which:
X and Y are each N;
Z is a single bond or an optionally substituted linking group;
R1 is hydrogen, or a substituent group, or the Y nitrogen is unsubstituted;
R2 is amino or a substituent group;
N* is amino when R1 is hydrogen or =NH when R1 is a substituent group; or
N* is a group NRaRb wherein Ra and Rb are independently H or an alkyl group; or
N* is an optionally substituted piperazinyl ring; and
A is a sulphur containing heterocycle substituted with halogen, alkyl or alkoxy.

8. The compound according to claim 7, wherein the sulphur containing heterocycle is optionally substituted with 1, 2, or 3 chlorine or bromine atoms.

9. The compound according to claim 7, wherein the compound is selected from the group consisting of:
3,5-Diamino-6-[3-(2,5-dichlorothienyl)]-1,2,4-triazine [CEN-071];
3,5-Diamino-6-[2-(3,4,5-trichlorothienyl)]-1,2,4-triazine [CEN-079];
5(3)-Amino-6-[3-(2,5-dichlorothienyl)]-2,3(2,5)-dihydro-3(5)-imino-2-methyl-1,2, 4-triazine [CEN-080];
5(3)-Amino-6-{2-(3,4,5-trichloro)thienyl}-2,3(2,5)-dihydro-3(5)-imino-2-methyl-1,2,4-triazine [CEN-194];
5(3)-Amino-6-{2-(3,4,5-trichloro)thienyl}-2,3(2,5)-dihydro-3(5)-imino-2-ethyl-1,2,4-triazine [CEN-195];
3,5-Diamino-6-[2-(4,5-dibromothienyl)]-1,2,4-triazine [CEN-122];
3,5-Diamino-6-[2-(5-bromothienyl)]-1,2,4-triazine [CEN-124];
3,5-Diamino-6-[2-(3-bromothienyl)]-1,2,4-triazine [CEN-125];
3,5-Diamino-6-[2-(5-chlorothienyl)]-1,2,4-triazine [CEN-138];
and
3,5-Diamino-6-[2-(3-chlorobenzo[b]thiophenyl)]-1,2,4-triazine [CEN-114].

10. The compound according to claim 7, wherein the compound is 3,5-Diamino-6-[2-(3,4,5-trichlorothienyl)]-1,2,4-triazine [CEN-079].

11. A pharmaceutical composition comprising a compound of claim 7 and a pharmaceutically acceptable carrier.

12. A pharmaceutical composition comprising a compound of claim 8 and a pharmaceutically acceptable carrier.

13. A pharmaceutical composition comprising a compound of claim 9 and a pharmaceutically acceptable carrier.

14. A pharmaceutical composition comprising a compound of claim 10 and a pharmaceutically acceptable carrier.

* * * * *